(12) United States Patent
Pendo et al.

(10) Patent No.: US 10,882,007 B2
(45) Date of Patent: Jan. 5, 2021

(54) LUMINAIRE WITH BIOFILTER

(71) Applicant: ABL IP Holding LLC, Conyers, GA (US)

(72) Inventors: Kathryn Margaret Pendo, Silver Spring, MD (US); David P. Ramer, Reston, VA (US); Jack C. Rains, Jr., Sarasota, FL (US); Min-Hao Michael Lu, Castro Valley, CA (US); James Benton French, Carmel, IN (US)

(73) Assignee: ABL IP HOLDING LLC, Conyers, GA (US)

( * ) Notice: Subject to any disclaimer, the term of this patent is extended or adjusted under 35 U.S.C. 154(b) by 117 days.

(21) Appl. No.: 15/986,119

(22) Filed: May 22, 2018

(65) Prior Publication Data

US 2019/0358584 A1 Nov. 28, 2019

(51) Int. Cl.
*F24F 13/078* (2006.01)
*B01D 53/84* (2006.01)
(Continued)

(52) U.S. Cl.
CPC ........... *B01D 53/84* (2013.01); *A61L 9/122* (2013.01); *B01D 53/007* (2013.01); *C12N 1/12* (2013.01);
(Continued)

(58) Field of Classification Search
CPC ............. F21V 33/0064; F24F 13/078; B01D 53/84–85
See application file for complete search history.

(56) References Cited

U.S. PATENT DOCUMENTS 3,846,072 A 11/1974 Patterson
5,089,413 A * 2/1992 Nelson ................. C12M 23/04
435/254.1
(Continued)

FOREIGN PATENT DOCUMENTS

CN 2218870 Y 1/1996
CN 203075284 U 7/2013
(Continued)

OTHER PUBLICATIONS

Anet et al., "Characterization and Selection of Packing Materials for Biofiltration of Rendering Odourous Emissions", Water Air Soil Pollut., 2013, vol. 224, No. 1622—13 pages.
(Continued)

*Primary Examiner* — Sean P Gramling
(74) *Attorney, Agent, or Firm* — RatnerPrestia

(57) ABSTRACT

Disclosed are examples of luminaires that provide light for general illumination and treat air via a biofilter. In the examples, a luminaire may include a light source configured to illuminate a space, a biofilter configured to treat air, and an air circulation system. The light source may be configured to illuminate a space in which the luminaire is located with general illumination light. The biofilter may include an air permeable membrane, a substrate, and a microorganism that treats air that comes in contact with the microorganism. The air circulation system is configured to draw air into contact with the biofilter and output air treated by contact with the biofilter into at least a portion of the space illuminated by the light source.

20 Claims, 12 Drawing Sheets

(51) Int. Cl.
  *F21V 33/00* (2006.01)
  *A61L 9/12* (2006.01)
  *C12N 1/20* (2006.01)
  *B01D 53/00* (2006.01)
  *C12N 1/12* (2006.01)

(52) U.S. Cl.
  CPC ............ *C12N 1/20* (2013.01); *F21V 33/0064* (2013.01); *F24F 13/078* (2013.01); *A61L 2209/12* (2013.01); *A61L 2209/14* (2013.01); *A61L 2209/22* (2013.01); *B01D 2259/802* (2013.01)

(56) References Cited

U.S. PATENT DOCUMENTS

| | | |
|---|---|---|
| 5,422,795 A | 6/1995 | Liu et al. |
| 6,471,136 B1 | 10/2002 | Chatterjee et al. |
| 7,815,327 B2 | 10/2010 | Shamshoian |
| 8,758,619 B2 | 6/2014 | Husain et al. |
| 8,772,744 B1 | 7/2014 | Liu |
| 2005/0058584 A1 | 3/2005 | Shyu |
| 2005/0220680 A1 | 10/2005 | Ma et al. |
| 2010/0196214 A1 | 8/2010 | Graff et al. |
| 2013/0094204 A1 | 4/2013 | Budai et al. |
| 2015/0151015 A1 | 6/2015 | Bugenske et al. |
| 2018/0058929 A1 | 3/2018 | Ramer et al. |

FOREIGN PATENT DOCUMENTS

| | | | |
|---|---|---|---|
| CN | 204986607 U | | 1/2016 |
| EP | 2778549 A2 | | 9/2014 |
| JP | 61174922 A | * | 8/1986 |
| KR | 101304139 B1 | * | 9/2013 |
| WO | 2015148025 A1 | | 10/2015 |

OTHER PUBLICATIONS

"A Review of Biofiltration Packing", https:/biofilters.com.webreview.htm, revised Aug. 15, 2013—8 pages.
Janni et al., "Evaluation of Biofiltration of Air—An Innovative Air Pollution Control Technology", ASHRAE Transactions, 2001, pp. 198-214.
Kennes et al., "Bioprocesses for Air Pollution Control", J. Chem. Technol. Biotechnol, 2009). vol. 84, pp. 1419-1436.
Prachuabmom, A., and Panich, N. "Isolation and Identification of Xylene Degrading Microorganisms from Biofilter." 2010, Journal of Applied Sciences, vol. 10, No. 7, pp. 585-589.
Yoshikawa et al. "Bacterial Degraders of Coexisting Dichloromethane, Benzene, and Toluene, Identified by Stable-Isotope Probing." 2017, Water Air Soil Pollut, vol. 228, No. 418, pp. 1-10.
Yoshikawa et al. "Biodegradation of Volatile Organic Compounds and Their Effects on Biodegradability under Co-Existing Conditions" 2017, Microbes Environ, vol. 32, No. 3, pp. 188-200.
Yoshikawa et al. "Integrated Anaerobic-Aerobic Biodegradation of Multiple Contaiminants Including Chlorinated Ethylenes, Benzene, Toluene, and Dichloromethane." 2017, Water Air Soil Pollut, vol. 228, No. 25, pp. 1-13.
Eltzov et al., "Bioluminescent Liquid Light Guide Pad Biosensor for Indoor Air Toxicity Measuring," Analytical Chemistry, 2015, vol. 87, pp. 3655-3661.
Estrada et al. "A Comparative study of fungal and bacterial biofiltration treating a VOC mixture." 2013, Journal of Hazardous Materials, vol. 250-251—pp. 190-197.
Aisyah et al., "Exploring the Potential of Whole Cell Biosensor: A Review of Environmental Applications," International Journal of Chemical, Environmental & Biological Sciences (IJCEBS), vol. 2, 2014, pp. 52-56.
Aizpuru et al., "Biofiltration of a Mixture of Volatile Organic Emissions", Journal of the Air & Waste Managament Association, (2001) vol. 51, No. 12—pp. 1662-1670
Baltrenas et al., "A Biochar-based Medium in the Biofiltration System: Removal Efficiency, Microorganism Propagation, and the Medium Penetration Modeling", Journal of the Air & Waste Management Association, (2016), vol. 66, No. 7, pp. 673-686.
Baltrenas et al., "Investigation into the Aerodynamic Process of Air Treatment using a Plate-type Biofilter", Environmental Technology, (2016), vol. 37, No. 5—pp. 569-576.
Bohrn et al., "Air Quality Monitoring Using a Whole-Cell based Sensor System," Procedia Engineering, vol. 25, 2011, pp. 1421-1424.
Bohrn et al., "Monitoring of Irritant Gas using a Whole-cell-based Sensor System," Sensors and Actuators B: Chemical, 175, Dec. 2012—pp. 208-217.
Dai et al., "Technology and Application of Microbial Biosensor," Open Journal of Applied Biosensor, 2013, vol. 2, pp. 83-93.
Gil et al., "A Biosensor for the Detection of Gas Toxicity Using Recombinant Bioluminescent Bacterium," Biosensors and Bioelectronics. Mar. 15, 2000—pp. 23-30.
Leson et al., "Biofiltration: An Innovative Air Pollution Control Technology for VOC Emissions", Journal of the Air & Waste Management Association, (1991), vol. 41, No. 8, pp. 1045-1054.
Repeckiene et al., "Succession of Microorganisms in a Plate-type Air Treatment Biofilter during Filtration of Various Volatile Compounds", Environmental Technology, (2015), vol. 36, No. 7, pp. 881-889.
Sandström et al., "Biosensors in Air Monitoring," J. Environ. Monit., 1999, vol. 1, pp. 293-298.
Ting et al., "Cyanobacterial Photosynthesis in the Oceans: The Origins and Significance of Divergent Light-harvesting Strategies", TRENDS in Microbiology, vol. 10, No. 3, Mar. 2002—pp. 134-141.
Priya et al., "Biodegradation of Dichloromethane Along with Other VOCs from Pharmaceutical Wastewater", App. Biochem Biotechnol., 2013, vol. 169, pp. 1197-1218.

* cited by examiner

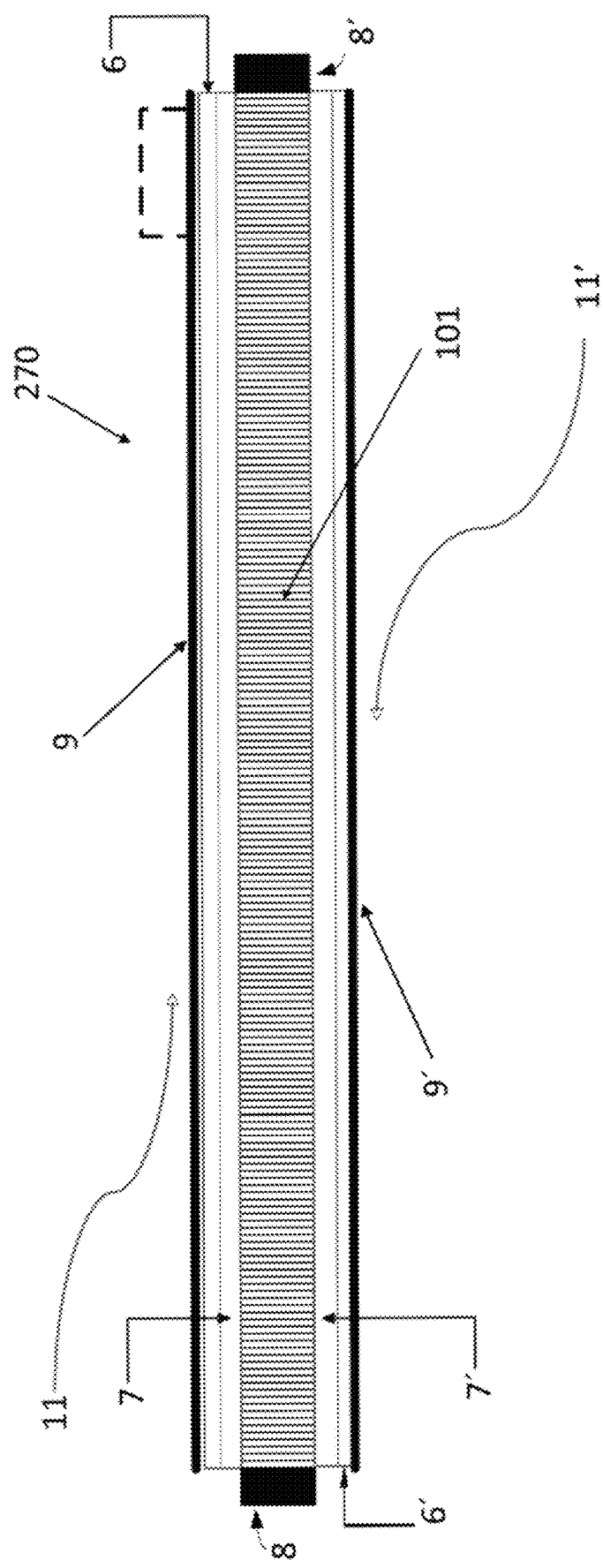

LUMINAIRE WITH BIOFILTER

TECHNICAL FIELD

In various examples, the present subject matter relates to a luminaire that utilizes microorganisms in the form of a biofilter to treat air in the environment in which the luminaire is located.

BACKGROUND

As awareness of the effects of the environment on people's health has increased, one area that has garnered greater attention is the quality of the air that people breathe. It is well documented that buildings may develop into "sick buildings" in which mold and other toxins may be present. For example, some work places, such as industrial areas and laboratories, may have toxic, or potentially toxic, chemicals, materials and gases present that may adversely affect the air quality within the work place. Other habitable spaces, such as hospitals, schools, and dormitories, may have airborne impurities and/or airborne bacteria.

There is a continuing need to improve air quality, especially indoor air in various spaces. For example, air pollutant removal or mitigation is an important goal. For example, carbon dioxide buildup can be problematic when too many people are present in a room. Removing the carbon dioxide and providing oxygen is highly desirable. Removing impurities and toxins from the air remains an important goal as furniture and floor materials can produce volatile organic compounds (VOCs) that are harmful or even toxic to people and animals.

SUMMARY

Hence, there is room for further improvement in air quality systems to provide treated air within a space.

Provided is an example of a luminaire that includes a light source configured to illuminate a space, a biofilter capable of treating air, and an air circulation system capable of drawing air into contact with the biofilter and outputting air treated by contact with the biofilter into at least a portion of the space illuminated by the light source.

An example of a system is also provided. The example system includes a luminaire and a controller. The luminaire including a light source configured to illuminate a space, a biofilter capable of treating air, and an air circulation system capable of drawing air into contact with the biofilter and outputting air treated by contact with the biofilter into at least a portion of the space illuminated by the light source. The controller is coupled to control light from the light source and control the air circulation system.

Also provided is an example of a method that includes emitting light from a light source in a luminaire to illuminate a space, drawing air into contact with a biofilter in the luminaire, where the biofilter treats the air, and outputting air treated by contact with the biofilter into at least a portion of the space illuminated by the light source.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accordance with the present concepts, by way of example only, not by way of limitations. In the figures, like reference numerals refer to the same or similar elements.

FIG. 3A illustrates an example of a biofilter usable in the luminaire example of FIG. 2.

DETAILED DESCRIPTION

Figure 1:
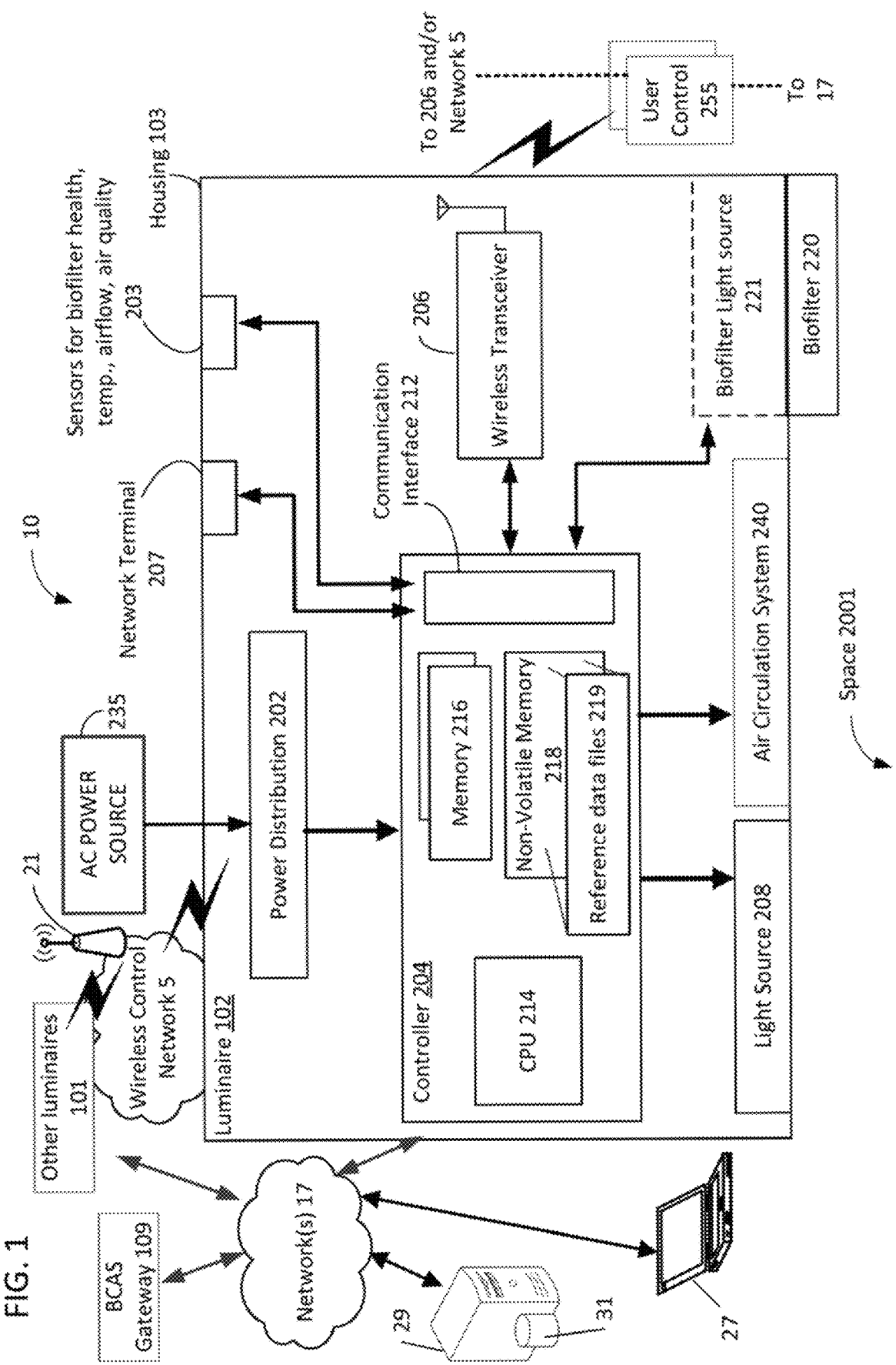
FIG. 1 illustrates a block diagram system example incorporating a luminaire containing a biofilter.

The examples described herein are directed to luminaires, e.g., light fixtures, which are able to remove impurities, volatile organic compounds (VOC) and the like from the environment in which the luminaire is located, to systems including one or more such luminaires and method of operating a luminaire or system. In addition to providing general illumination light for a habitable area, the example luminaires are capable of treating air in a desired manner as described in more detail herein.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The examples below relate to improved hardware and techniques for combined general illumination and biofilters configured to treat air in proximity to a location of a luminaire. In a simple example, a system may include a luminaire and a controller. The luminaire includes a light source and a biofilter. The controller may be incorporated in the luminaire or separate from the luminaire. Systems, however, may include some number of luminaires controlled by one controller or systems involving a number of networked controllers and luminaires associated with or incorporating the controllers. Systems may also include or communicate with other relevant equipment such as environmental monitoring devices, heating, ventilation and air conditioning (HVAC) equipment, and/or higher layer computer equipment such as various user terminal devices on or off the premises and/or a building control and automation system (BCAS).

The term "luminaire," as used herein, is intended to encompass essentially any type of device that processes energy to generate or supply artificial light, for example, for general illumination of a space intended for occupancy or observation, typically by a human that can take advantage of or be affected in some desired manner by the light emitted from the device. However, a luminaire may provide light for use by automated equipment, such as sensors/monitors, robots, etc. that may occupy or observe the illuminated space, instead of or in addition to light provided for a human. In most examples, the luminaire(s) illuminate a space or area of a premises to a level useful for a human occupant in or passing through the space, e.g. general illumination of a room, a corridor in a building or of an outdoor space such as a street, sidewalk, parking lot, performance venue or the like.

The general illumination light output of a luminaire, for example, may have an intensity and/or other characteristic(s) that may satisfy an industry acceptable performance standard for a general illumination lighting application. The lighting performance standard for the general illumination may vary for different uses or applications of the illuminated space, for example, as between residential, office, manufacturing, warehouse, hospital, nursing home, or retail spaces.

Terms such as "artificial lighting," as used herein, are intended to encompass essentially any type of lighting that a device produces by processing of electrical power to generate the light. An artificial lighting device, for example, may take the form of a lamp, light fixture, or other luminaire that incorporates suitable light sources, where each light source by itself contains no intelligence or communication capability, such as one or more light emitting diodes (LEDs) or the like, or a lamp (e.g. "regular light bulbs") of any suitable type.

In several illustrated examples, such a luminaire may take the form of a light fixture, such as a pendant, a drop light, a downlight, a wall wash light, or the like. Of course, other fixture-type luminaire mounting arrangements are possible. For example, at least some implementations of the luminaire may be surface mounted to or recessed in a wall, ceiling or floor. Orientation of the example luminaires and components thereof are shown in some of the drawings and described below by way of non-limiting examples only. The luminaire with the lighting component(s) may take other forms, such as lamps (e.g. table, floor, or street lamps) or the like. Additional devices, such as fixed or controllable optical elements, may be included in the luminaire, e.g. to distribute light output from the light source in a particular manner.

Terms such as "lighting device" or "lighting system," as used herein, are intended to encompass essentially any combination of an example of a luminaire discussed herein with other elements such as electronics of a controller and/or support structure, to operate and/or install the particular luminaire implementation. Such electronics hardware, for example, may include some or all of the appropriate driver(s) for the illumination light source, an additional light source if any for separately supplying light to the microorganism(s) used in the biofilter, any associated control processor or alternative higher level control circuitry, and/or data communication interface(s). The electronics for driving and/or controlling the lighting component(s) may be incorporated within the luminaire or located separately and coupled by appropriate means to the light source component(s) of the luminaire.

As used herein, the term "biofilter" refers to an assembly that treats air in a manner desired by the user by the action of one or more microorganisms contained within the biofilter. Biofilters are well-known in the art and generally refer to devices that remove pollutants from the air by a biological operation of a microorganism, algae or the like. The biofilters of the examples described herein can be used for this purpose. However, as used herein, the term "biofilter" is not limited to only removing components from air. In some examples, the biofilters described herein may also add a desired component to the air, e.g., a desired odor, or to replace a removed component with a desired component, e.g. to replace carbon dioxide with oxygen, as discussed below with reference to the respective examples.

The term "treating air" generally means that a microorganism, such as bacteria, algae, or fungi, modifies or conditions the air that comes into contact with the microorganism in a desired manner. That is, the microorganism, is capable of changing the composition of the air as desired by the user. This process may also be referred to as "conditioning air."

The disclosed examples are now described in more detail with reference to the drawings.

FIG. 1 is a functional block diagram illustrating details of a luminaire incorporating a biofilter as described herein. One example the luminaire 102 may include a light source 208 configured to illuminate a space 2001, a biofilter 220 capable of treating air, and an air circulation system 240 capable of drawing air into contact with the biofilter 220 and outputting air treated, for example, by contact with the biofilter 220 into at least a portion of the space 2001 illuminated by the light source 208.

The system example of FIG. 1 illustrates a luminaire 102 equipped with a biofilter positioned within an air pathway. The system 10 may include or other luminaires 101, which may or may not be similarly equipped, as appropriate to both provide suitable general illumination and to provide the appropriate level of biological air treatment at the space. The air pathway (shown in other examples) may be a duct (also shown in other examples) that guides air from a space in which the luminaire 102 is located to the biofilter and out of the duct as treated or conditioned air.

The space 2001 may be any location or locations serviced for lighting and other purposes by a system 10 of the type described herein. Hence, the example of system 10 may provide lighting, air treatment and possibly other services in a number of service areas in or associated with a building, such as various rooms, hallways, corridors or storage areas of a building (e.g., home, hospital, office building, schools, and an outdoor area associated with a building). Any building forming, or at, the premises, for example, may be an individual or multi-resident dwelling or may provide space for one or more enterprises and/or any combination of residential and enterprise facilities.

The system elements, in a system like system 10 of FIG. 1, may include any number of luminaires, such as luminaires 102 or 101 one or more of which may be equipped with a biofilter. Luminaire 102 is an example of a luminaire suitable for use in a system of luminaires as described herein that is equipped with a biofilter 220. The luminaire 102 includes a controller 204 that may be configured to control lighting related operations, e.g., ON/OFF, intensity, brightness or color characteristic of the output of the light source 208, and possibly other lighting related functions of the luminaire 102. In addition, controller 204 may be configured to provide biofilter (e.g. health or functional) and/or environmental (e.g. air quality) status monitoring and control of functions related to the proper operation of the biofilter 220, as described in greater detail below.

The controller 204 of the luminaire 102 may send commands to the other luminaires 101 that are executed by processing elements, such as controller 204 present in the other luminaires 101. Conversely, the controller 204 of the luminaire 102 may receive and execute commands from another luminaire 101 or from another control device in the system 10 or in communication with the system 10.

The system elements 101 and 102 in a system like system 10 of FIG. 1, may be coupled to and communicate via a data network 17 at the space 2001. The data network 17 in the example may be coupled to one or more luminaires via either a wired or wireless access point (WAP) (not shown) that couples to the network terminal 207 or to the wireless transceiver 206 to support communications at a premises (not shown in this example) including the space 2001. Such communications may be via wired and/or wireless communication media, e.g. cable or fiber Ethernet, Wi-Fi, Bluetooth, cellular or short range mesh. In many installations, there may be one overall data communication network 17 at the premises. For example, the network 17 may enable a user terminal for a user to control operations of luminaire 102 (or other luminaires 101). Such a user terminal is depicted in FIG. 1, for example, as a computing device 27, although any appropriate user terminal such as a mobile device may also be utilized. Network(s) 17 includes, for example, a local area network (LAN), a metropolitan area network (MAN), a wide area network (WAN) or some other private or public network, such as the Internet.

System 10 in the example also includes server 29 and database 31 accessible to a processor of server 29. Although FIG. 1 depicts database 31 as physically proximate server 29, this is only for simplicity and no such requirement exists. Instead, database 31 may be located physically disparate or otherwise separated from server 29 and logically accessible by server 29, for example via network 17.

Database 31 may be a collection of reference data files for use in conjunction with the biofilter 220. For example, each reference data file within database 31 may include reference data related to the health and growth of the microorganisms of a particular type of biofilter, status of air flow and biofilter light sources and/or other components of the luminaire that influence or respond to the operation of the biofilter, or the like. The reference data files may include image data, sensor (e.g. optical, air flow, air quality, temperature or the like) threshold values, or other reference materials that may provide an indicator of the health, growth or status of the microorganisms that forms each available type of biofilter that may be used in a luminaire. In one example, a selected reference data file from among the collection of reference data files is loaded into a memory of the luminaire 102 (or other luminaires 101) for the particular type of biofilter included as biofilter 220 in that luminaire; and the luminaire 102 (or other luminaires 101) may be configured to utilize the selected reference data file to determine the status of the biofilter 220 and possibly control one or more components of the system 10 to achieve intended air treatment results via the biofilter 220. That is, the selected reference data enables luminaire 102 (or other luminaires 101) to indicate when the biofilter is operating properly, needs replacement, inspection or servicing (e.g. replacement of nutrients, replacement of biofilter light source, or the like). As another example, the elected reference data may enable luminaire 102 (or other luminaires 101) to respond to sensed condition(s) to control the air circulation system 240 and/or a biofilter light source 221 to modify filtration through the biofilter 220.

The luminaire 102 (or other luminaires 101) may have different configurations, and may be implemented using different and/or similar components.

An example of a luminaire 102 is shown in FIG. 1 where the luminaire 102 includes a housing 103, a light source 208 for general illumination, the biofilter 220, a controller 204, a wireless transceiver 206, air circulation system 240, and a wired network terminal 207. The communication interface 212 may be coupled to a data communication network, such as 17, via either the wireless transceiver 206, the wired network terminal 207, or both. The controller 204 has an internal processor configured as a central processing unit (CPU) 214, a memory 216, a non-volatile memory 218 and the communication interface 212. The processor 214 is coupled to the memories 216 and 218 and the communication interface 212; and the communication interface 212 provides communications for the controller 204 with the light source 208, the biofilter 220 and other luminaire components such as the wireless transceiver 206 and the network terminal 207.

In the example of FIG. 1, any of the reference data files that have been installed in the controller 204 are shown stored in non-volatile memory 218. Of course, either of the memories 216 or 218 may store those reference data files and program instructions for analyzing the biofilter 220 and/or controlling any systems operations related to operation of the biofilter 220. The luminaire 102 may receive a reference data file via the network 17, either the wireless transceiver 206 or the network terminal 207 and the communication interface 212. The reference data file may include information related to data output from one or more of airflow sensors, air quality sensors, imaging sensors (e.g., cameras, photodiodes or the like), a spectrometer, a micro-electro-mechanical (MEM) sensor (e.g. pressure sensor), algae growth monitor, nutrient supply monitor or the like. Examples of a luminaire incorporating a spectrometer are disclosed in U.S. patent application Ser. No. 15/247,076, the entire contents of which are incorporated herein by reference.

The processor forming the core of CPU 214, when executing the stored program instructions, is configured to perform various functions related to the analysis of signals generated by the sensors 203 and control of any relevant system operations. The processor in 214 and associated memories 216 and 218 in the example of the luminaire 102 may be components of the controller 204, which may be a microchip device that incorporates the CPU as well as one or more memories. The controller 204 may be thought of as a small computer or computer-like device formed on a single chip (e.g. a system-o-a-chip (SOC)). Alternatively, the processor forming the CPU 214 and the memory 216 or 218 may be implemented as separate components, e.g. by a microprocessor, ROM, RAM, flash memory, etc. coupled together via a bus or the like. The housing 103 may serve to protect the components of the luminaire 102 from the dust, dirt, water (e.g. rain) or the like in the location in which the device is installed.

Also included in the example luminaire 102 is a power distribution unit 202 configured to receive power, in the example, from an external alternating current (AC) power source 235. The power distribution unit 202 may, for example, be configured to distribute electrical power to the various components within the luminaire 102. For example, the light source 208 is an artificial light generation device (such as an LED group or array, or the like) configured to generate illumination light upon consumption of electrical power from the power distribution unit 202.

This example of the luminaire 102 includes the capabilities to communicate over one or more radio frequency (RF) bands, although the concepts discussed herein are applicable to control devices that communicate with luminaires and other system elements via a single RF band. Hence, in the example, the luminaire 102 includes a wireless transceiver 206, which may be configured for sending/receiving control signals, for sending/receiving sensor data signals, and/or for sending/receiving pairing and commissioning messages. For example, the transceiver 206 may be one or more transceivers configured as a sub-GHz transceiver; and for such an implementation, a variety of control signals are transmitted over the sub-GHz control band of the wireless control network 5, including, for example, signals for turn lights on/off, dim up/down, set scene (e.g., a predetermined light setting), and sensor trip events. WiFi, BLE or other frequencies/protocols may be used for the control network 5 and transceiver 206 instead of or in addition to the sub-GHz band example. Alternatively, the same transceiver 206 or a second transceiver (not shown) may be configured as a 2.4 GHz transceiver for Bluetooth low energy (BLE) that carries various messages related to commissioning and maintenance of a wirelessly networked lighting system. The wireless transceiver 206 coupled to the communication interface 212 and to a wireless network, such as 5 via the wireless access point 21 of FIG. 1. The wireless transceiver 206 may be, for example, configured to transmit signals related to outputs from the sensor 203 and/or operations of biofilter 220 from the processor 214 to a computing device, such as such as devices 29 and/or 27 of FIG. 1, external to the environment in which the luminaire 102 is located.

In the example of FIG. 1 luminaire 102 is shown as having one processor 214, for convenience. In some instances, the luminaire may have multiple processors. For example, a particular device configuration may utilize a multi-core processor architecture.

In general, the controller 204 of the luminaire 102 controls the various components or devices included in the luminaire 102, such as the light source 208 and the biofilter 220, connected to the controller 204. For example, controller 204 may control one or more included RF transceivers 206 to communicate with other RF devices (e.g. wall switches, sensors, commissioning device, etc.). In addition, the controller 204 controls the light source 208 to turn ON/OFF automatically, or at the request of a user. In addition, controller 204 controls other aspects of operation of the light source 208, such as light output intensity level, or the like.

For example, the controller 204 may be responsive to signals received from various control devices coupled to the system 10. An example of a control device is a user control, such as 255. The user control 255 may also be coupled to the controller 204 of luminaire 102 or the control 255 may communicate with the luminaire, for example, via wireless communication with transceiver 206. The user control 255 may be configured to output signals related to lighting ON/OFF, dimming control, heating, ventilation, and air conditioning (HVAC) that may be provided to the luminaire 102 and/or to the building control and automation system (BCAS) gateway 109. The BCAS gateway 109 may be a centralized controller of a building system such as HVAC, physical security, lighting, elevators and the like.

In the example luminaire 102, the controller 204 may also be coupled to an air circulation system 240 and a biofilter light source 221 (optional) of the biofilter 220. The air circulation system 240 may include ducting and a fan that are configured to transport air from the environment in which the luminaire 102 is located toward the biofilter 220 for treatment of the transported air, and return the treated air to the environment in which the luminaire is located. Alternatively or in addition, the air circulation system 240 may be coupled to an HVAC system (not shown) which may transport air into the ducting in place of, or to supplement, the air transported by the fan in the air circulation system 240.

The system 10 may include one or more sensors 203. The sensors 203 may either be sensors external to the luminaire 102 (not shown) or sensors internal to the luminaire 102. Examples of suitable sensors 203 may include airflow sensors, air quality sensors, imaging sensors (e.g., cameras, photodiodes or the like), algae growth monitors, nutrient supply monitors or the like. Although not separately shown, the system 10 may include sensors related to lighting control, such as occupancy sensors, ambient light sensors, temperature of light sensors located/configured to provide feedback related to operation of the light source 208, etc.

The controller 204 may also control operation of the biofilter light source 221. For example, the controller 204 may perform the general functions of turning the biofilter light source 221 ON or OFF, adjusting the intensity and/or color characteristic of the light emitted by the biofilter light source 221. Alternatively, the biofilter light source 221 may remain ON continuously since electrical power is received from electrical AC mains, such as AC power supply 235 in which case, power conservation may not be a design constraint. Alternatively, the biofilter light source 221 may be controlled to remain ON/OFF for predetermined periods of time, such as 12 hours light/dark cycles for normal photosynthetic function, or for a shorter time period to provide limited light which controls a growth rate of the algae. The biofilter light source 221 may be one or more light emitting diodes (LED) that emit light in the blue (approximately 450-495 nanometers) and red (approximately 620-750 nanometers) wavelengths to promote photosynthesis. In some examples, the biofilter light source 221 may be optional.

The luminaire 102 may couple to a network, such as network 17 or 5 of FIG. 1, for wired communication through the network terminal 207 and/or connected for wireless communication wireless transceiver 206. In the example, internally, the network terminal 207 and the wireless transceiver 206 connect through the interface 212 to communicate with the CPU 214 of the controller 204.

The luminaires 101 and 102 may take various forms. It may be helpful to discuss an example of a general arrangement of a luminaire suitable for use as luminaires 101 or 102.

Figure 2:
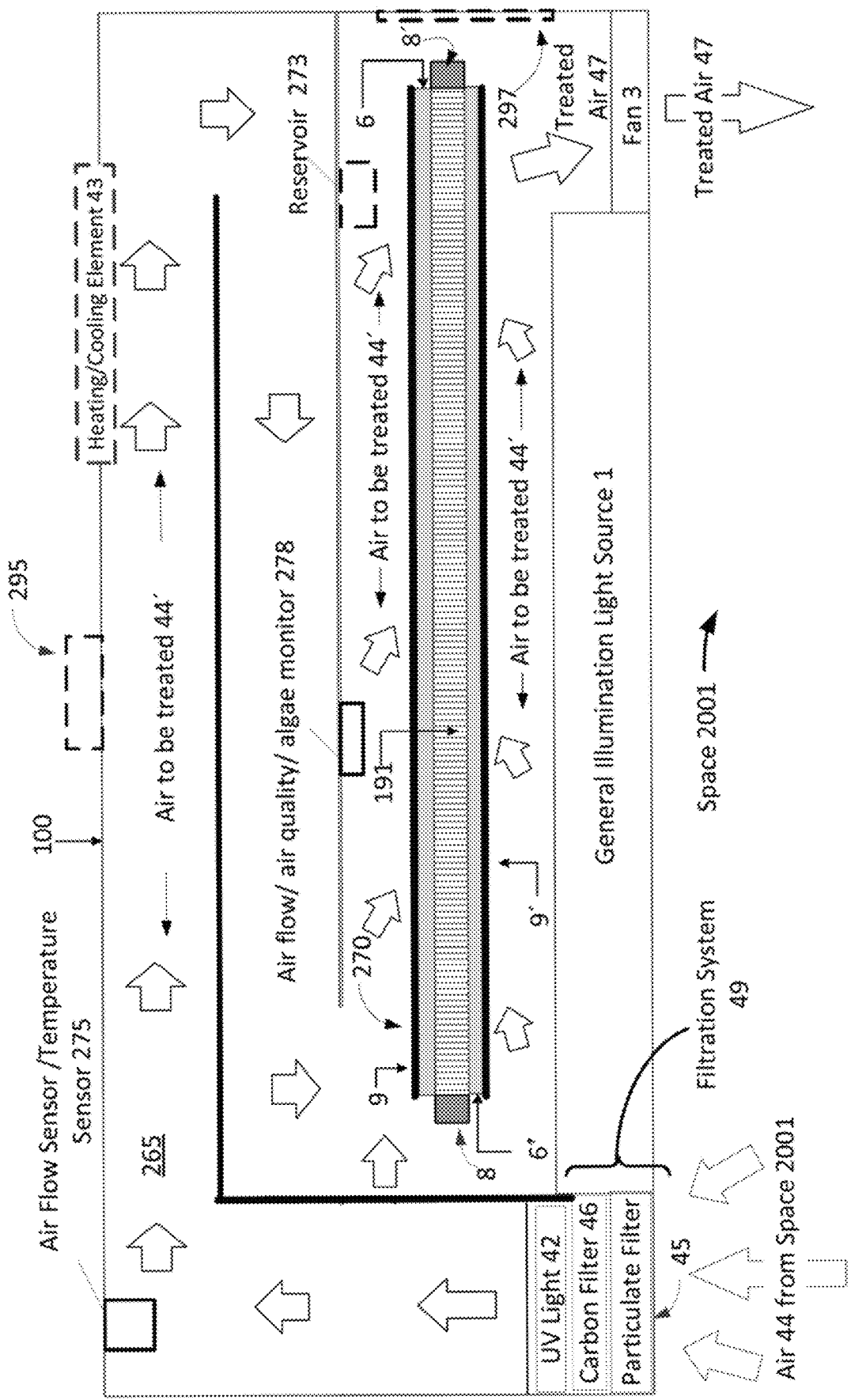
FIG. 2 illustrates a cross sectional view of an example of a luminaire containing a biofilter.

FIG. 2 illustrates a cross sectional example of a luminaire containing a biofilter. The example luminaire 100 includes a general illumination light source 1, a biofilter 270, ducting 265, sensors 275 and 278, and a fan 3. In this example, the light source 1 may be configured to illuminate a space, such as space 2001. The light source 1 may be a general illumination light source configured to illuminate the space 2001 in which the luminaire 100 is located. Although not shown in the present example, the light source 1 may include multiple light sources, such as a general illumination light source directed to emit light into space 2001 as well as an ultraviolet (UV) or near UV light source that functions as a germicide and irradiates air and/or surfaces in the space 2001.

The biofilter 270 is capable of treating air via, for example, contact of air with the biofilter or by passage of the air through the biofilter. An air circulation system (e.g. to implement system 240 in FIG. 1) may include ducting 265 and the fan 3. The fan 3 may be configured to draw air from space 2001 into the ducting 265. The fan 3 may be a single fan or may be a number of fans that cooperate to draw air into the ducting 265 and distribute the air over a surface of the air permeable media 9 and 9' of the biofilter 270. The fan 3 and ducting 265 enable the drawn in air to contact with the microorganism(s) of the biofilter 270. One example of the fan 3 may be a system of fans that controllably cooperate to draw untreated air into contact with microorganisms on the substrate and outputting air following treatment of the air by the microorganism or algae. Such a fan system may, for example, include a number of fans of the same or different airflow capacities (e.g. measured in cubic feet per second/minute or the like). Within the ducting 265 may be structural supports in a particular location of the ducting 265 that positions the biofilter 270 within the air flow path to allow the air to be treated 44' to come into contact with the biofilter 270.

The air circulation system 240 of FIG. 1 may also be supplemented with or replaced with an environmental control system. The environmental control system may be configured to condition the air in order to maximize the ability of the microorganisms to treat the air as described herein. The environmental control system may include a humidifying system, a temperature control system, a filtration system, such as 49, or any combination thereof. The filtration system 49 may include, for example, an ultraviolet (UV) light source 42 as well as filters, such as a particulate filter 45 that filters particles and a carbon filter 46 for removal of odors, and the like.

Optional components of the luminaire 100 may include one or more attachment points 295 for use in securing the luminaire 100 when the luminaire 100 is implemented as a pendant light, sconce-like fixture, a wall-wash implementation, or the like. In another optional example, the luminaire 100 may also include an access port 297. The biofilter 270 may be configured to be inserted into and removed from the luminaire 100 via the access port 297, e.g. for installation and/or replacement. Alternatively or in addition, the access port 297 may be configured to (1) add a liquid medium (not shown in this example) to the substrate 6 or 6', (2) remove a liquid medium from the substrate 6 or 6', (3) add a liquid medium to the substrate 6 or 6' and remove a liquid medium from the substrate 6 or 6'. In another example, the luminaire 100 may also contain a replaceable or refillable liquid reservoir 273. In one example, the liquid contained in the reservoir contains an aqueous medium that provides nutrients and other substances for maintaining the viability of the microorganism or algae. The reservoir 273, in some examples, may be a dual chamber container in which a first container contains the aqueous medium while the second chamber may be configured to contain waste materials from the microorganisms. The ducting 265 of the luminaire 100 may also include a heating/cooling element 43 that may be coupled to and controlled by the controller 204 of FIG. 1. The heating/cooling element 43 may be configured to either heat or cool the air to be treated 44' as the air moves through the ducting prior to contacting the biofilter 270.

The air to be treated 44' interacts with the biofilter 270 (e.g. by contact with microorganisms (not shown in this example) of the biofilter 270) after which the treated air 47 is returned to at least a portion of the space 2001 illuminated by the light source 1. The air brought in contact with the biofilter 270 is treated and output to at least a portion of the space 2001 illuminated by the light source 1. In this example, the interaction of the air to be treated 44' with the biofilter may be simple contact as the light guide 191, which may be a solid structure, may prevent treated air 47 from passing through the biofilter 270.

In the example of FIG. 2, the biofilter (270) includes a first substrate (6) and a second substrate (6'). The first substrate 6 includes a first microorganism (not separately shown in this example), and the second substrate 6' includes a second microorganism (not separately shown in this example). The microorganisms on the respective substrates 6 and 6' are described below in more detail with reference to another example.

In the example of FIG. 2, the biofilter 270 may be configured to be receive illumination from one or more biofilter light sources (8 and 8'). The biofilter light sources (8 and 8') may have specifications the same as or similar to those discussed with respect to biofilter light source 221 of FIG. 1. The biofilter light sources (8 and 8') may be configured to illuminate via a light guide (191) configured to distribute the light via one or more output surfaces of the guide to the microorganisms in substrates 6, 6' of the biofilter 270. The light guide 191 may be configured to evenly distribute the light emitted from the biofilter light source 8, 8'.

The biofilter 270 in the FIG. 2 example may also include a first air-permeable membrane (9) and a second air-permeable membrane (9'). The air-permeable membranes 9 and 9' may be hydrophobic. Suitable materials for the membrane, such as 9 and 9', include silicones and fluoropolymers, such as Teflon®. The membranes 9 and 9' may also be composed of Tyvek® or GOR-TEX®.

The flow of the air to be treated 44' through the ducting 265 may come into contact or pass through the biofilter 270. The air treatment functions of the biofilter 270 are discussed in more detail with reference to other examples. It may be appropriate at this time to discuss the biofilter 270 in more detail with reference to FIG. 3.

FIG. 3A illustrates an example of a biofilter usable in the luminaire examples of FIG. 1 or 2. FIG. 3 shows air flow (11) and (11') across the first substrate 9 and the second substrate 9'. The first substrate 6 includes a first microorganism (7), and the second substrate 6' includes a second microorganism (7'). The respective microorganisms 7 and 7' are described below in more detail with reference to another example.

In another example, the substrate is contained in a panel containing the biofilter that is capable of being installed in the luminaire and the panel with the substrate may later be removed from the luminaire. For example, the biofilter may be an enclosed environment with the nutrient substrate medium and microorganisms, and the entire biofilter may be removed from the luminaire for replacement or refurbishment.

The luminaire, such as 100, may be configured to house the biofilter so that the air circulation system can draw air into contact with the biofilter and return treated air after contact with the biofilter. In some examples, the luminaire has a slot or holder into which the biofilter can be inserted.

In some examples, the biofilter is in the form of a "cartridge" or "cassette" that can be easily inserted and removed from the luminaire, much in the same way that disposable air filters are used in household furnaces. In some examples, the cartridge or cassette is formed from a metal, plastic or paper material.

Figure 3B:
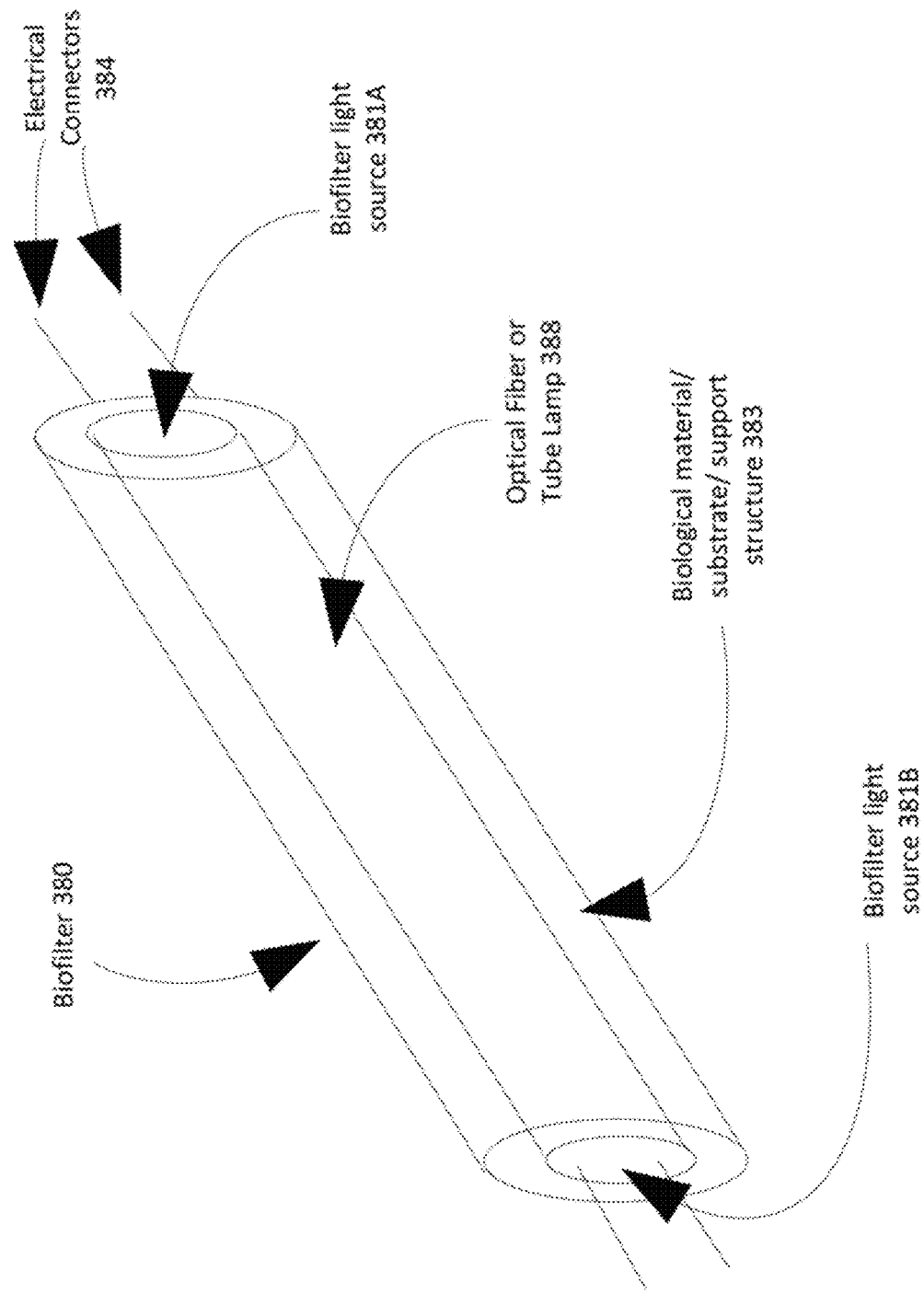
FIG. 3B illustrates a plan view of an example of a cylindrical biofilter configuration suitable for use in the luminaire examples of FIGS. 1 and 2.

FIG. 3B illustrates a plan view of an example of a cylindrical biofilter configuration. In the example of FIG. 3B, the biofilter 380 may include biofilter light sources 381A and 381B that emit light into an optical fiber/tube lamp 388. The biofilter light sources 381A and 381B may be configured to output light suitable for promoting growth of microorganisms, which include bacteria and algae. The optical fiber/tub lamp 388 may be substantially surrounded by the microorganisms/substrates and support structures (the details of which are described with reference to other examples). Electrical connectors 384 may be coupled to the biofilter light sources 381A and 381B and to a processor or LED light driver that controls the light emissions of the respective light sources 381A and 381B.

Figure 3C:
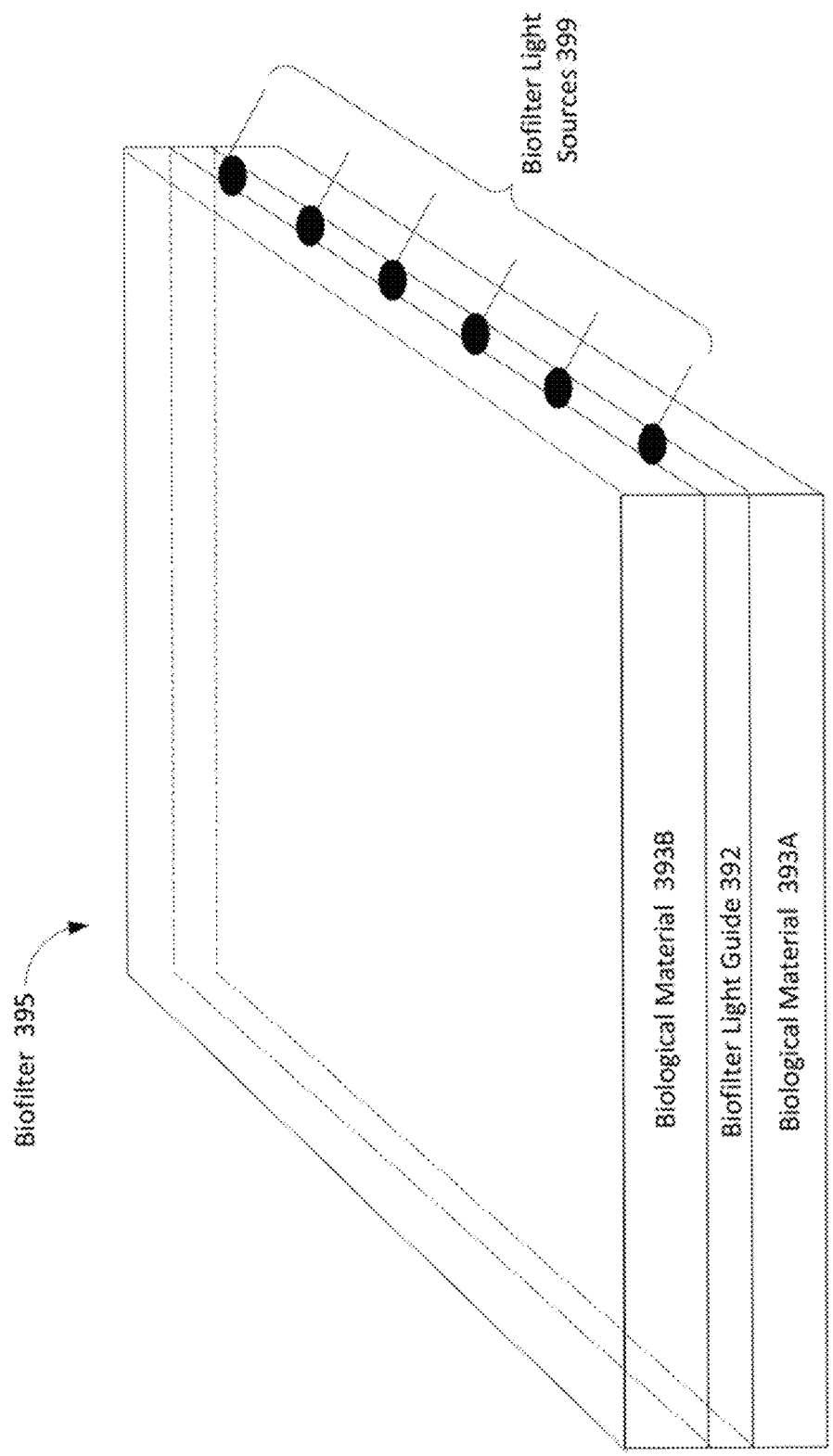
FIG. 3C illustrates a plan view of a rectangular biofilter configuration suitable for use in the luminaire examples of FIGS. 1 and 2.

FIG. 3C illustrates a plan view of a rectangular biofilter configuration. The biofilter 395 may be configured with a biofilter light guide sandwiched between two microorganism layers 393A and 393B. The microorganisms forming the microorganism layers 393A and 393B may be the same or different. For example, both microorganism layers 393A and 393B may be green algae or the like. Alternatively, one layer, such as microorganism layer 393A, may be green algae, while the other layer, such as microorganism layer 393B, may be a bacteria, algae or fungi. The biofilter light guide 392 may be configured to distribute light emitted by the respective biofilter light sources 399. The biofilter light sources 399 may be LEDs such as those described with respect to the examples of FIGS. 1-3A. The biofilter light guide 392 may be configured to distribute the emitted light substantially evenly over the surfaces of both microorganism layers 393A and 393B.

The biofilter in the examples described herein, such as 220, 270, or 395 may be used for treating air, where the air flows over and/or through an air-permeable substrate containing a microorganism, such as 7 and 7'. Representative examples of biofilters and/or packing materials used therein are described in (1) Anet et al., "Characterization and Selection of Packing Materials for Biofiltration of Rendering Odourous Emissions," Water Air Soil Pollut (2013), 224, 1622, (2) "A Review of Biofiltration Packings," revised Aug. 15, 2013 on the World Wide Web at biofilters.com/webreview.htm, (3) U.S. Pat. No. 8,758,619, (4) Estrada et al. "A Comparative study of fungal and bacterial biofiltration treating a VOC mixture." 2013, Journal of Hazardous Materials, 250-251, 190-197, (5) Kennes et al. "Bioprocesses for air pollution control." 2009, J Chem Technol Biotechnol, 84, 1419-1436, (6) Prachuabmom, A., and Panich, N. "Isolation and Identification of Xylene Degrading Microorganisms from Biofilter." 2010, Journal of Applied Sciences, 10, 7, 585-589, (7) Priya, V. S., and Philip, L. "Biodegradation of Dichloromethane Along with Other VOCs from Pharmaceutical Wastewater." 2013, Appl Biochem Biotechnol, 169, 1197-1218, (8) Yoshikawa et al. "Integrated Anaerobic-Aerobic Biodegradation of Multiple Contaminants Including Chlorinated Ethylenes, Benzene, Toluene, and Dichloromethane." 2017, Water Air Soil Pollut, 228, 25, 1-13, (9) Yoshikawa et al. "Bacterial Degraders of Coexisting Dichloromethane, Benzene, and Toluene, Identified by Stable-Isotope Probing." 2017, Water Air Soil Pollut, 228, 418, 1-10, and (10) Yoshikawa et al. "Biodegradation of Volatile Organic Compounds and Their Effects on Biodegradability under Co-Existing Conditions" 2017, Microbes Environ, 32, 3, 188-200. The entire contents of each of which are incorporated herein by reference.

In one example, the microorganism 7 and 7' is capable of removing carbon dioxide from the air. In another example, the microorganism 7 and 7' is capable of adding oxygen to the air. In another example, the microorganism 7 and 7' is capable of removing carbon dioxide from the air and capable of adding oxygen to the air. In yet another example, the microorganism 7 and 7' is capable of removing a volatile organic compound (VOC) from the air. In a specific example, the microorganism 7 and 7' is capable of removing ammonia from the air. In one or more examples, the products of VOC degradation are water-soluble.

Another application of the luminaire as described herein is the addition of odors to the air, i.e., the microorganism 7 and 7' is capable of adding an odor to the air. For example, the odor may be an odor that has a pleasant effect such as the odor of baking bread or cookies. This would be useful as to maintain a crowd of people in an area as the pleasant odor would encourage people to remain in the area. Conversely, in some applications, for example, to keep an area free of loiterers, it may be beneficial if the microorganism 7 and 7' were to add an unpleasant odor to the air. This would be useful as a crowd control technique as the unpleasant odor would encourage people to leave the area and/or stay out of the area because of the unpleasant odor.

As discussed above with reference to the examples of FIGS. 1 and 2, the luminaires 100 and 102 may contain a live microorganism 7 or 7' that is capable of treating air. The identity of the microorganism is not particularly limited. In one example, the microorganism may be capable of photosynthesis.

A variety of different microorganisms 7 and 7' may be used in the biofilter 270. It should be noted that the microorganisms 7 and 7' may be the same or different. For example, three classes of microorganisms that are very useful are bacteria, algae, and fungi. The microorganisms, bacteria and green algae are especially useful. Bacteria tend to have rapid uptake of substrate and subsequent growth, but can be more sensitive to environmental conditions. Fungi grows more slowly and tend to have a smaller surface area, but can withstand harsher conditions. Anaerobic and aerobic microorganisms may also be beneficial, but access for the anaerobic microorganisms to the toxins in the air may be problematic. Some anaerobic species can survive in an oxygen environment for an extended period of time.

Cyanobacteria are a phylum of bacteria that obtain their energy through photosynthesis. Cyanobacteria are useful because they remove carbon dioxide from the air and produce oxygen via photosynthesis. Thus, cyanobacteria treat air by removing carbon dioxide and adding oxygen to the air that contacts the cyanobacteria in the biofilter.

Figure 4:
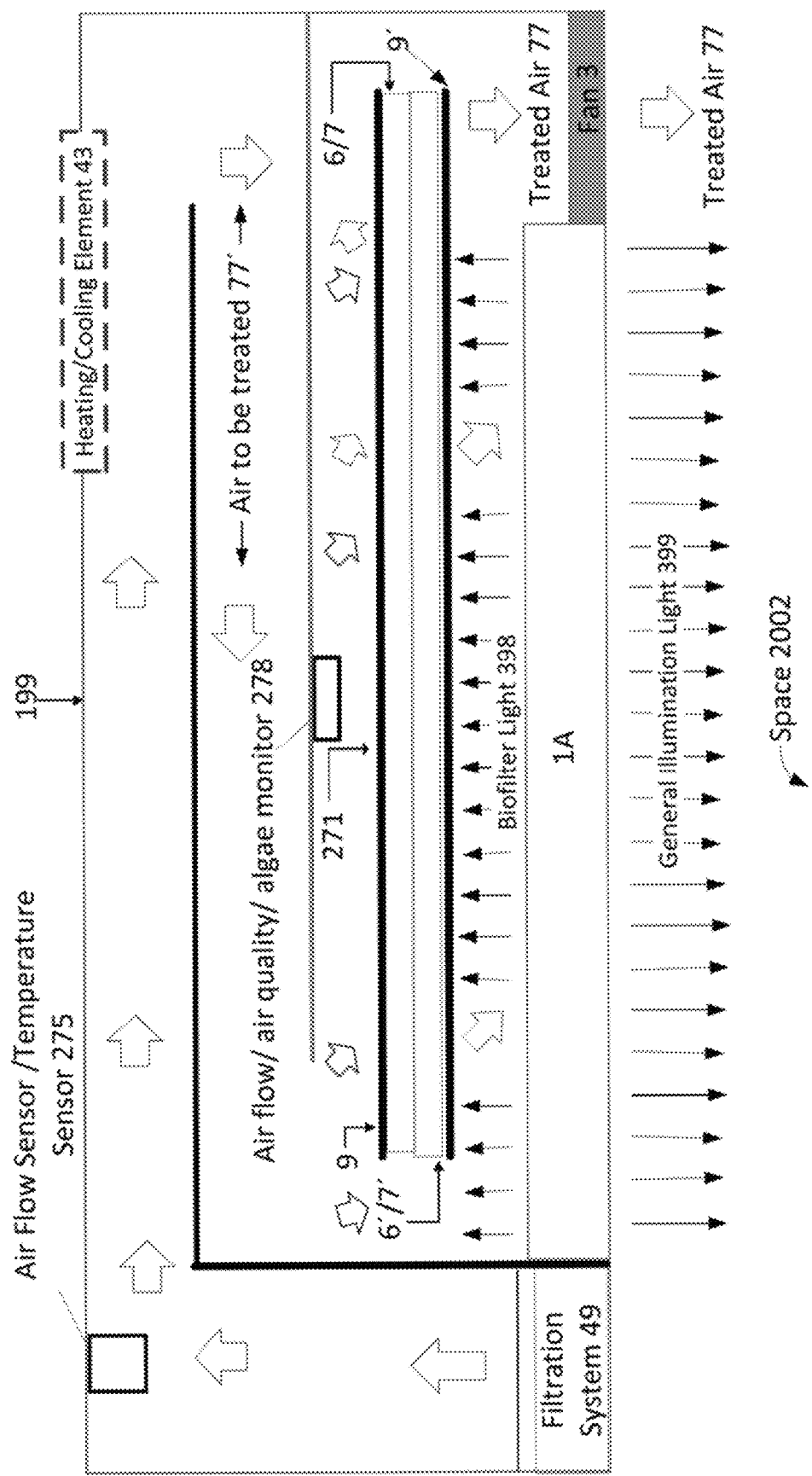
FIG. 4 illustrates another cross sectional view of an example of a luminaire containing a biofilter different from the biofilter of FIG. 2.

Since cyanobacteria are capable of photosynthesis, this microorganism needs a source of light to drive this process. The light required for photosynthesis may be provided by either the biofilter light sources, such as the biofilter light sources 8 and 8' described above with respect to FIG. 2, or the general illumination light source as shown in FIG. 4. In the example of FIG. 4, the luminaire 199 may include elements similar to luminaire 100 of FIG. 2, such as a filtration system 49, ducting 265, sensors 275 and 278, and a fan 3. Elements having similar reference numbers, such as heating/cooling element 43, in FIG. 2, may also have similar functions and a detailed discussion of the respective element will not be repeated for sake of brevity. However, in contrast to the biofilter light source 8 and 8' of FIG. 2 that may be configured provide the light for growing the cyanobacteria. The example of FIG. 4 may provide a general illumination light source 1A that is configured to emit light into the ducting 285 under and/or around biofilter 271. The biofilter 271 may have air permeable substrates 9 and 9', substrates 6 and 6', and microorganisms 9 and 9', but may not be coupled to separate biofilter light sources, such as 8 and 8' of FIG. 2.

The air to be treated 77' interacts with the biofilter 271 (e.g. by contact with microorganisms 7 and 7' of the biofilter 271) after which the treated air 77, is returned to at least a portion of the space 2002 illuminated by the light source 1A. The air to be treated 77' may either go around the biofilter 271 or through the biofilter 271, and after contact with the microorganism may be considered treated air 77.

Figure 5:
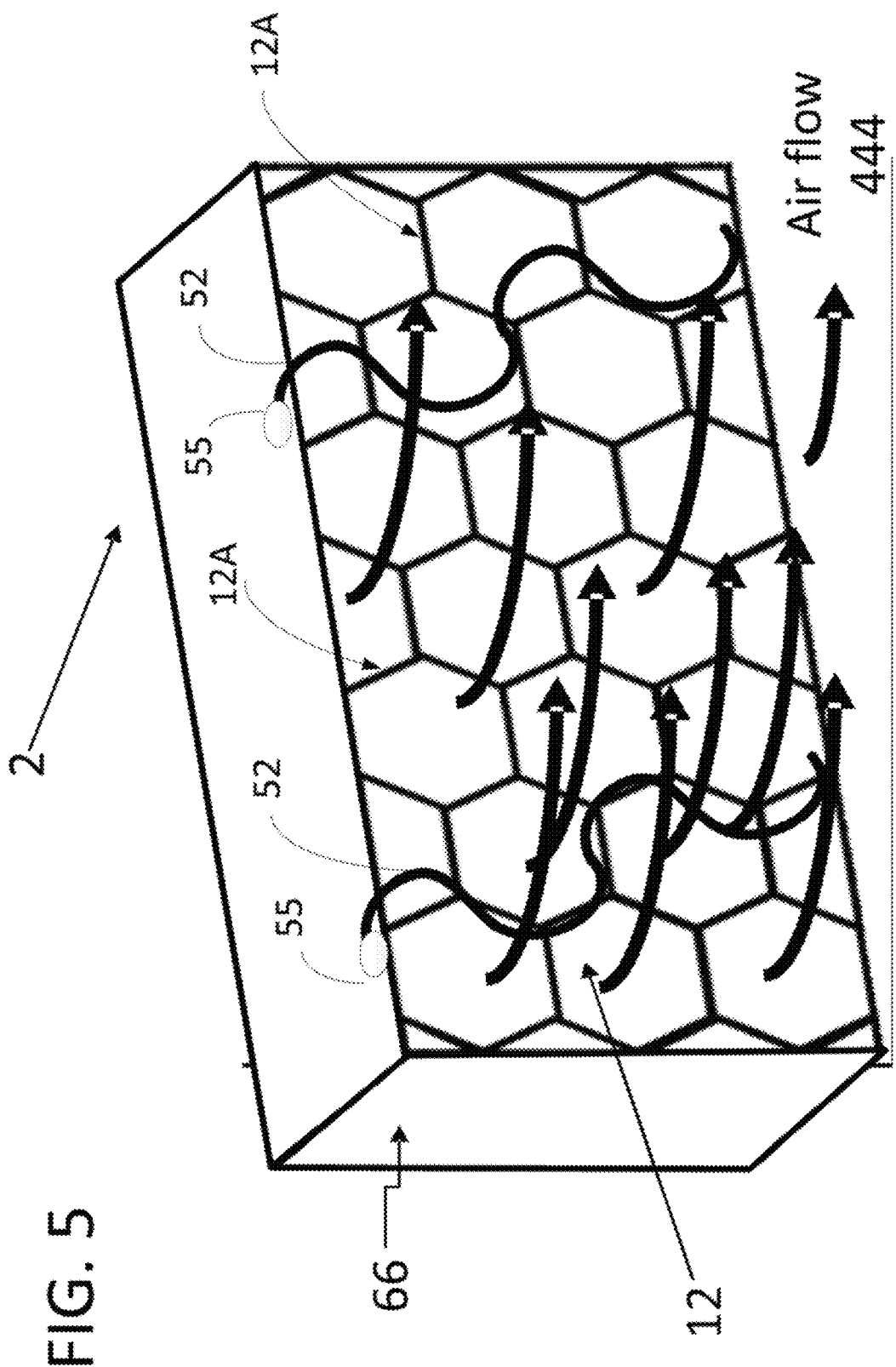
FIG. 5 illustrates a plan view of an example of a biofilter having a honeycombed substrate.
Figure 6:
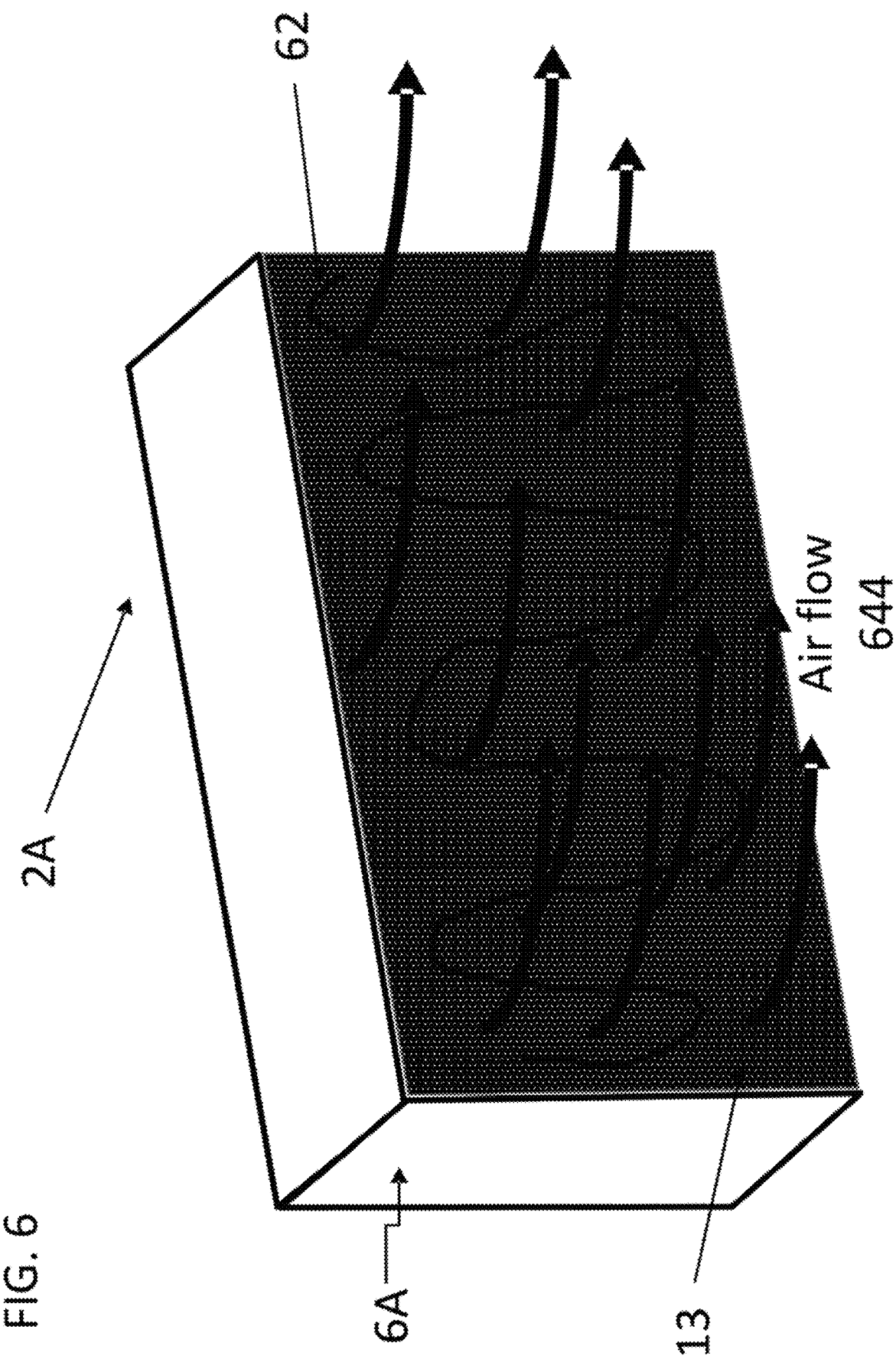
FIG. 6 illustrates a plan view of an example of a biofilter with a substrate having an open fiber component structure and a fiber optic light source.

Examples of suitable configurations for biofilter 271 are shown in FIGS. 5 and 6. Instead, the general illumination light source 1A may emit general illumination light 399 into the space 2002 and also emit biofilter light 398 toward the biofilter 271. The biofilter light 398 and general illumination light 399 may be light of the same wavelength that provides light suitable for photosynthesis in the cyanobacteria of biofilter 271. For example, the wavelength of light provided by the general illumination light source 1A may be in approximate ranges suitable for enabling growth of viable cyanobacteria within the biofilter 271.

As mentioned above, photosynthetic-capable microorganisms, such as green algae, may also be used in the biofilters 270. The term "green algae" embraces a large group of algae consisting of the Chlorophyte and Charophyte algae. There are about 8,000 species of green algae. Green algae contain chloroplasts that are capable of photosynthesis.

Examples of bacteria that produce what is generally considered a "good" or "desirable" odor include *Pseudomonas aeruginosa* (grape-like odor, sweet, fruity, flowery, smells like taco chips, tortillas or corn chips), *Staphylococcus lugdenensis* (sweet, hay-like, earthy odor), *Streptococcus anginosus* (sweet, cake-like, caramel, butterscotch odor), *Escherichia coli* (floral/flowery odor), *Haemophilus influenza* (flowery odor), *Candida*/Yeast (yeasty, like bread baking or beer), *Eikenella corrodens* (bleach), Actinomycetes, *Streptomyces, Nocardia* spp (a rich, earthy, musty dirt scent after fresh rain), and *Candida albicans* ("yeasty" on blood agar, like bread baking or like beer).

Examples of bacteria that produce what is generally considered a "bad" or "undesirable" odor include Gram-negative anaerobes (bad breath, morning breath, sulfur smells), *Acinetobacter baumannii* (dirty gym socks or a gym locker), *Proteus* spp (rancid, like rotten chicken soup or broth). These may be incorporated should the intent of the installer be that people do not loiter or linger in the space around the luminaire. For example, this may be helpful for use in public areas that need to be vacant at night, pedestrian traffic bottlenecks, passage ways to secure areas, or the like.

A variety of microorganisms for removing VOC from air are well-known. Representative examples of such microorganisms include *Actinomyces* sp., *Aminobacter* sp., *Arthrobacter* sp., *Bacillus* sp., *Candida* sp., *Cephalosporium* sp., *Hansenula* sp., *Hyphomicrobium* sp., *Methylobacterium* sp., *Methylophaga* sp., *Methylophilus* sp., *Micrococcus* sp., *Micromonospora* sp., *Mucor* sp., *Mycobacterium* sp., *Ovularia* sp., *Paracoccus* sp., *Penicillum* sp., *Pseudonocardia* sp., *Pseudomonas* sp., *Streptomyces* sp., *Thiobacillus* sp., and *Xanthomons* sp.

The substrate, such as 6 and 6', may be implemented in a number of different configurations. In some examples, the biofilter includes a substrate that is suitable to maintain the viability of the microorganism. Considerations for selecting the substrate may include (1) the ability to retain moisture to sustain the microorganism and especially a biofilm layer as described herein, (2) a large surface area, both for contaminant absorption and growth of the microorganism, (3) the ability to retain nutrients and supply them to microorganism as required, (4) low resistance to air flow (minimizes pressure drop and air circulation power requirements), or (5) physical characteristics, such as physical stability and ease of handling. The air flows over the surface of or through the substrate 6 and 6' so that the microorganism 7 and 7' may condition the air. The air may, in some examples, flow over the surface of the substrate 6, 6' and through the substrate 6, 6'.

Generally, the substrates 6 and 6' may include any material that may structurally support the microorganism 7, 7' and remain permeable to the air to be treated. In some examples of the luminaire 100, the support has a high surface area which is covered by the microorganism. In an example of the luminaire, the microorganism forms a biofilm over the support. An example of a suitable material is an alginate.

The substrates 6 and 6' may have pores which facilitate the flow of air. The pore size is not particularly limited and is preferably 1 to 5 times the size of the microorganism 7, 7'. A preferred pore size is 1 to 10 μm in substrate examples that contain pores.

The substrates 6 and 6' in some examples have a packed bed (not shown) containing a packing material. The microorganism in such examples may be located in and/or on the packed bed. For example, the microorganism may be in the form of a biofilm on the packed bed. Examples of the packing material may include, for example, glass particles, ceramic particles, gravel particles, plastic particles, activated charcoal, or a combination thereof. Particles in the form of beads are especially suitable. The packing material (not shown) may, for example, be compost, soil, heather, peat or the like. In the example, the microorganism generally grows on or over the packing material.

In one example, the support for the microorganism within the biofilter is a replaceable hydrogel. Commonly used components of hydrogels include alginates (see, for example, Eltzov et al., "Bioluminescent Liquid Light Guide Pad Biosensor for Indoor Air Toxicity Measuring," Analytical Chemistry, 2015, 87 3655-3661), polyvinyl alcohol, sodium polyacrylate, acrylate polymers and copolymers thereof with an abundance of hydrophilic groups. Natural hydrogel materials may also be used, such as agarose, methylcellulose, hyaluronan, Elastin like polypeptides and other naturally derived polymers. The hydrogel may be overlaid on a substrate, such as 6 of FIG. 2, and be replaced after some time period. In another example, the substrate 6, microorganism 7, and the air permeable membrane 9 of the biofilter 270 may be formed from a hydrogel, and be removable from the light guide and be replaced with a new replacement substrate 6, microorganism 7, and the air permeable membrane 9 may be inserted into the biofilter 270 after some predetermined time period.

In another example, the substrate may contain a wicking material. In yet another example, the substrate may be composed of a hollow fiber membrane. In some examples, a biofilm formed from the microorganism may form on the hollow fiber membrane.

In some of the examples, the substrate 6 and 6' may contain a medium, such as water and nutrients, to provide continued viability and sustenance for the microorganisms, such as algae and cyanobacteria. The medium may be referred to as a liquid medium or an aqueous medium. This medium may also function to contain waste products produced by the microorganism. Examples of nutrients include carbohydrates, proteins, peptides, amino acids, lipids, vitamins, inorganic salts, and co-factors. A specific example of a suitable nutrient is glucose. The components of such media are well-known in the art.

Most nutritional media contains 1.5% agar and 0.5% peptone. In an example, where the microorganism may use the carbon in the VOCs, the VOCs may not need a supplemented carbon source (such as glucose or malt). Most bacteria thrive in pH neutral medium, while yeast and molds prefer acidic, 5.4-5.6 pH. The VOCs and degraded bacteria/fungi may thrive on a solid substrate medium. For example, the substrates 6 and 6' may include a nutritional material that may act as a solidifying agent that forms a solid medium substrate.

In some examples, the substrate is maintained at a moisture content of 30% to 60% in order to support the population of the microorganism. The liquid component discussed herein may also contain a chemical buffer in order to control pH. A preferred chemical buffer pH is around 7.0.

The flow rate of air across and/or through the substrate, such as 6 and 6', and thus the residence time may vary widely. The "residence time" represents the amount of time the microbes are in contact with the contaminated air stream, and is defined, for example, by void volume/volumetric flow rate or the like. Consequently, longer residence times produce higher efficiencies; however, a design can minimize residence time to allow the device to accommodate larger flow rates. For example, the residence time may range between 30 seconds to 1 minute.

The pressure drop across the substrate, such as 6 and 6', may be minimized since an increase in pressure drop requires more air circulation and can result in air channeling through the media (e.g. microorganisms). The pressure drop may be directly related to the moisture content in the media and the media pore size. Increased moisture and decreased pore size may result in increased pressure drop. Consequently, media filter selection and watering may be relevant to evaluating the performance and energy efficiency of the luminaire, such as 100 or 102. For example, the pressure drops may range between 1 and 10 hPa. In addition, the air permeability of air permeable surfaces such as 9 and 9' may also be considered.

In some examples, the substrate may contain more than one layer containing a microorganism. For example, the substrate may contain two or more different layers where different microorganisms are present in each layer. An example of a biofilter containing such a structure is shown in FIG. 3 as described above. The microorganisms may be the same or different. If the microorganisms are different, this provides for the possibility of different air treatments from the same device. For example, a microorganism which removes carbon dioxide from the air and adds oxygen could be used in combination with a different microorganism that removes VOCs from the air.

Different structure configurations are contemplated for supporting the microorganisms. FIG. 5 illustrates a plan view of an example of a biofilter having a honeycombed substrate. In the example of FIG. 5, the substrate 66 comprises a honeycomb structure 12 in which the walls 12A of the honeycomb structure 12 include the support material containing the microorganism that may also include packing material as described above. The honeycomb structure 12 enables air to flow through, as shown by air flow 444, the substrate 66 while providing a large surface area on which the microorganism may thrive and be in contact with the air. The honeycomb walls 12A of substrate 66 may optionally include a light guide and source, such as, for example, a fiber optic illuminator 52 and light source 55 that provide light to the microorganism (not shown in this example). The example of FIG. 5 is but one example, other examples of biofilter substrates 66 are also contemplated.

FIG. 6 illustrates a plan view of an example of a biofilter with a substrate having an open fiber component structure. An example of a biofilter (2A) that includes an open fiber structure (13) as a component of substrate (6A) is shown. The substrate 6A may include an optional fiber optic illuminator (62) that provides light to the microorganism (not shown in this example). The open fiber component structure of the substrate 6A enables air flow 644 through the open fiber structure (13).

In the example, a substrate 6A may include an exposed fiber structure formed from support material containing the microorganism as included in the packing material described above. The substrate 6A may also include a light guide (e.g., a fiber optic illuminator 62) that provides light for the microorganism (not shown in this example).

In each of the examples shown in FIGS. 5 and 6, the respective substrates are shown with a light guide (e.g. 52 and 62, respectively) that may assist in providing light to the microorganism for the promotion of photosynthesis. In some examples, the light guides 52 or 62 may be located between two or more different layers of the microorganism, as discussed above. Of course, the light guides may be used as biofilter light sources 221, 8 and 8' as shown in the examples of FIGS. 1-3.

Figure 7:
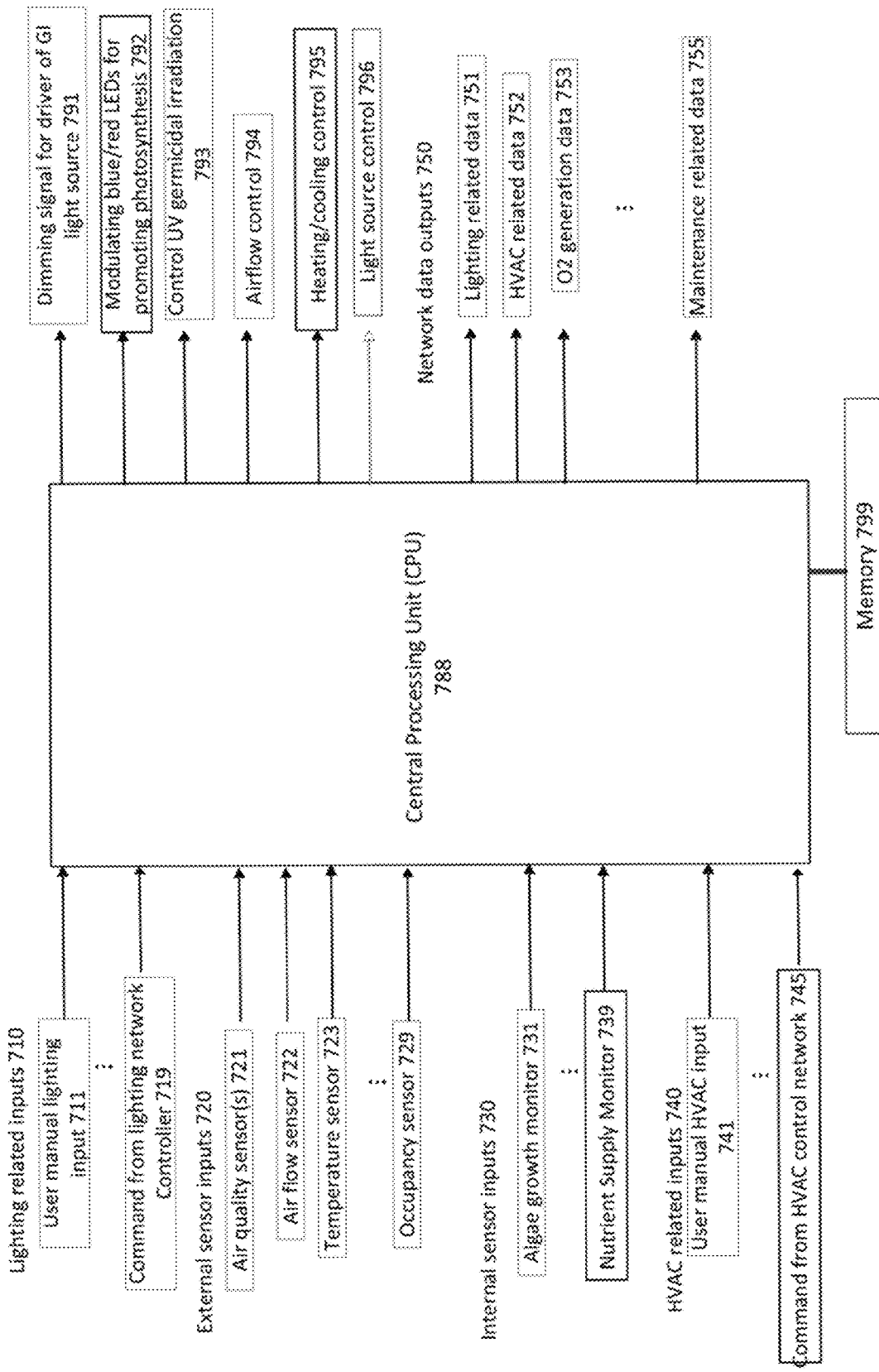
FIG. 7 illustrates a diagram of an example of a central processing unit for controlling operation of an example of a luminaire, such as those described with reference to FIGS. 1, 2 and 4.

It may now be beneficial to describe in more detail the control of the air treatment and lighting capabilities of the luminaire described in the foregoing examples. As shown in the example of FIG. 1, luminaire 102 includes the processor 204 for control of the lighting and air treatment operations. FIG. 7 illustrates a diagram of an example of a central processing unit for controlling operation of an example of a luminaire, such as those described with reference to FIGS. 1, 2 and 4.

The central processing unit (CPU) 788 of FIG. 7 (also referred to as a "processor") may be coupled to a number of different systems, sensors, and computing devices, such as 27 and 29 of FIG. 1. For example, the CPU 788 may receive lighting related inputs 710, external sensor inputs 720, internal sensor inputs 730, and HVAC related inputs 740. The computing devices may rely on the outputs from the CPU 788 to determine the status of the luminaire or information related to air quality or the like.

The luminaire examples described herein may be used to provide general illumination light and treat air in the space in which the luminaire is located. The CPU 788 may be configured to provide functions, such as controlling: (1) emission of light from a general illumination light source in the luminaire to illuminate a space, (2) the drawing of air into contact with a biofilter in the luminaire for treatment of the air when the air contacts the biofilter; and (3) outputting air treated by contact with the biofilter into at least a portion of the space illuminated by the light source.

The CPU 788 may be configured to perform the above control functions as well as other functions by executing programming code stored in the memory 799. The memory 799 may be one or more memories, such as 216 and 218 of FIG. 1. The CPU 788 may be configured upon execution of the programming code to respond to and/or process the respective inputs. For example, the lighting related inputs 710 may include user manual lighting inputs 711, commands from a lighting network controller 719, or the like. The external sensor inputs 720 may, for example, include air quality sensors 721, air flow sensors 722, temperature sensors 723, an occupancy sensor 729, or the like. The internal sensor inputs 730 may, for example, include an algae growth monitor 731, nutrient supply monitor 739, or the like. The HVAC related inputs may include user manual HVAC inputs 741, commands from the HVAC control network 745 (e.g., BCAS gateway 109 of FIG. 1).

The manual user inputs for lighting (i.e. 711) and HVAC (i.e. 741) may be provided by a user control, such as 255 of FIG. 1. Based on the different inputs, the CPU 788 may be configured to output one or more signals. For example, the CPU 788 may output a dimming signal to the driver of the general illumination source to dim or increase the intensity of the general illumination light emitted by the general illumination light source (shown in other examples). In addition, the CPU 788 may output signals specific to the air treatment functions, such as modulating the blue/red LEDs 792 of the biofilter light source for promoting photosynthesis, and airflow control 794. In response to and user manual lighting inputs 711, the CPU 788 may control the respective light sources to perform the task requested by the inputted request, such as a light source control 796 function (e.g., ON/OFF) or a dimming signal 791 function. Alternatively, the CPU 788 may output a light source control 796 signal in response to an input from an occupancy sensor 729 input. In addition, the CPU 788 may respond to inputs 719 from a lighting network controller or the like, such as a BCAS gateway or other luminaire via a wireless control network, by outputting a dimming signal 791 or a light source control 796 signal.

For example, in response to user manual HVAC inputs 741, the CPU 788 may output a heating/cooling control 795 signal for execution of the requested function associated with the user input. Alternatively, the CPU 788 may output a heating/cooling control 795 signal in response to an input from temperature sensor 723 input. In some examples, the heating/cooling control 795 may control the heating/control element 43 in the ducting as shown in FIGS. 2 and 4. The CPU 788 may output other potential control signals, such as controlling, if available, a UV light source, such as 42 of FIG. 2, that outputs germicidal irradiation 793. The CPU 788 may also control the airflow (794) in response to one or more inputs, for example, from the air quality sensor(s) 721 and/or airflow sensor 722.

The luminaire CPU 788 may be configured with programming to provide one or more features additional to the features described above. In examples in which the microorganism is capable of photosynthesis, which may benefit from the additional biofilter light source having a wavelength of 400 to 500 nm and/or 600 to 700 nm. For example, the additional biofilter light source may include modulating light emitting diodes that emit blue and/or red light for promoting photosynthesis.

The CPU 788 may also output data for use by computing devices, such as 27 and 29, connected to the luminaire. For example, the computing devices may receive network data outputs 750 such as lighting related data 751, HVAC related data 752, oxygen (02) generation data or maintenance related data 755.

Figure 8:
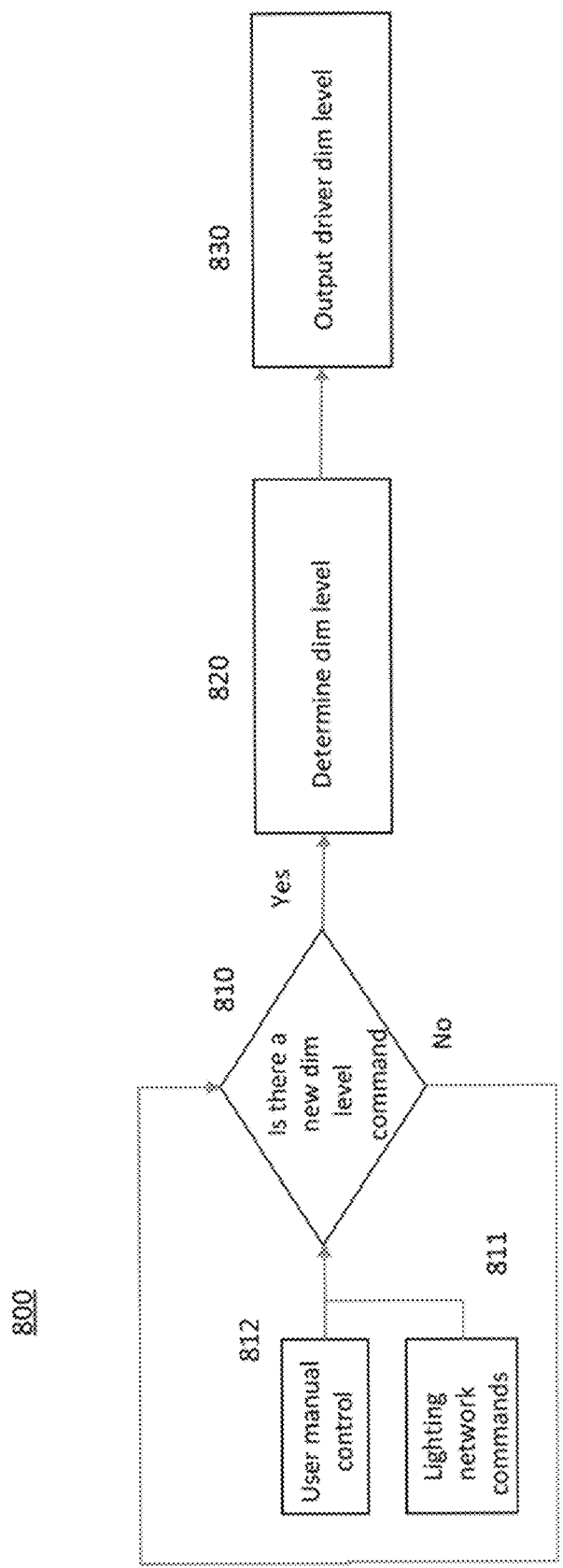
FIG. 8 illustrates an example of a control algorithm for controlling the intensity of the general illumination light output from the luminaire, such as the luminaire example of FIG. 1.

The CPU 788 upon execution of the programming code stored in the memory 799 may also perform control algorithms related to the dimming signals 791, such as the example described with respect to the flowchart of FIG. 8. FIG. 8 illustrates an example of a control algorithm for controlling the intensity of the general illumination light output from the luminaire, such as the luminaire example of FIG. 1. The process 800 is an example of a process that may be implemented upon execution of the programming in memory 799 by the CPU 788. The CPU 788 may review the input received user manual control signal 812 or lighting network command 811 to determine, at 810, whether there is a new dim level command. Conversely, if the determination is NO, there is no new dim level command, the CPU 788 may continue to review inputs received via 811 and 812. In the determination is YES, there is a new dim level command received from either 811 or 812, the CPU 788 may process the received signal to determine the dim level 820. Upon determination of the dim level, the CPU 788 may output a driver dim level 830 signal for implementing the requested dim level. Note that dim level may be either a reduced or an increase in general illumination or biofilter light intensity.

Figure 9:
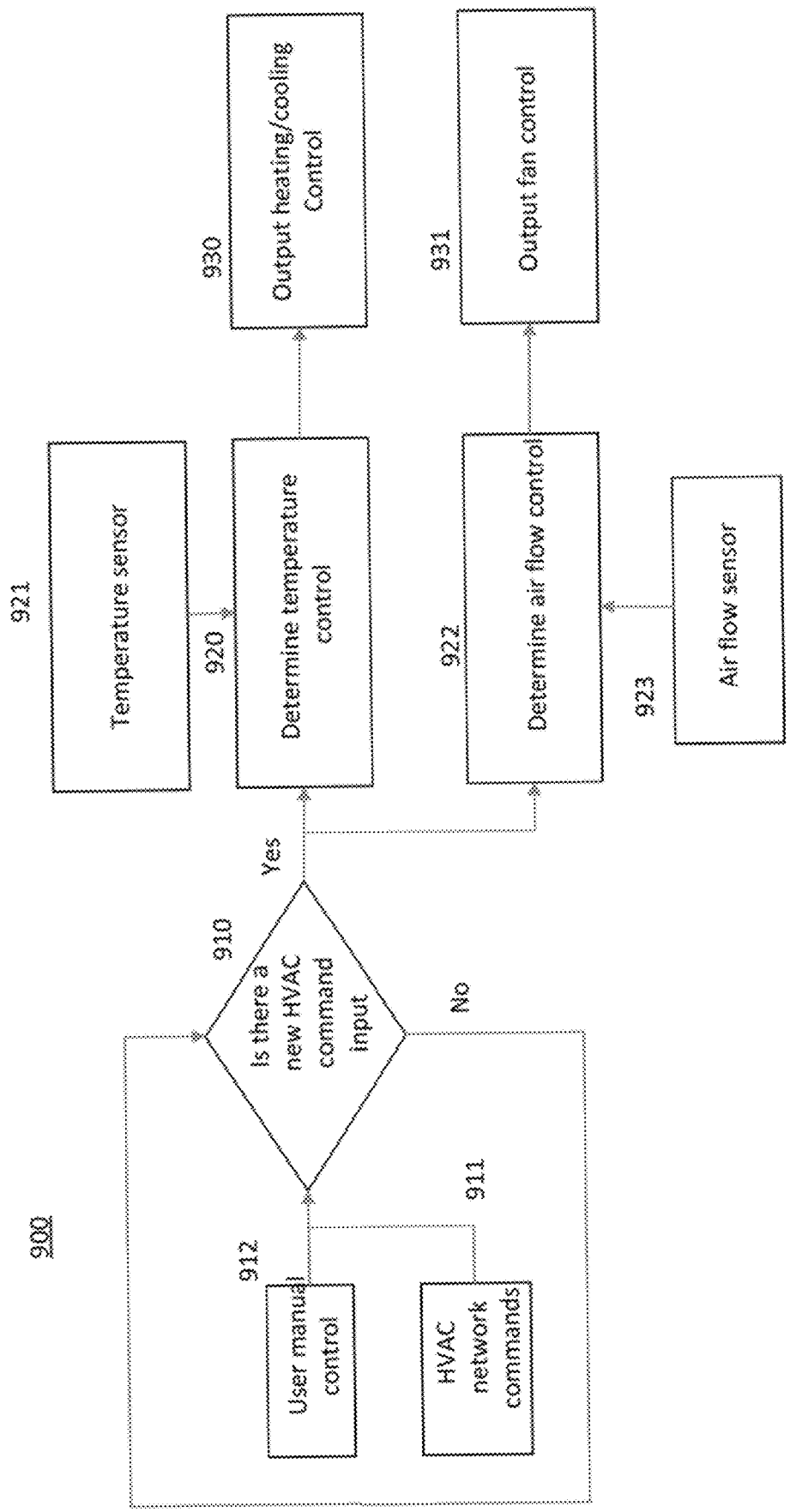
FIG. 9 illustrates an example of a control algorithm for controlling building operations via components of the luminaire, such as the example luminaire shown in FIG. 1.

FIG. 9 illustrates an example of a control algorithm for controlling building operations via components of the luminaire, such as the example luminaire shown in FIG. 1. In this example, the process 900 is an example of a process that may be implemented upon execution of the programming in memory 799 by the CPU 788. The CPU 788 may review the input received user manual control signal 912 or HVAC network command 911 to determine, at 910, whether there is a new HVAC command input. If the determination is NO, there is no new HVAC command input, the CPU 788 may continue to review inputs received via 911 and 912. Conversely, if the determination is YES, there is an HVAC command received from either 911 or 912, the CPU 788 may process the received signal to determine the temperature control 920 and to determine the air flow control 922. To determine whether a temperature setting adjustment in response to the temperature control 920 is necessary, a present temperature is determined based on an input from temperature sensor at 921. In response to the present temperature, the CPU 788 determines at 920 the heating/cooling control signal 930 that needs to be output based on the received inputs 911 or 912. Upon determination of, for example, a difference between the input from the temperature sensor 921 and an input received from either 911 or 912, the CPU 788 may output a heating/cooling control signal 830.

In addition, if the determination is YES, there is an HVAC command received from either 911 or 912, the CPU 788 may process the received signal to also determine the air flow control 922. To determine whether an airflow control setting adjustment is needed in response to the temperature control 920, a present airflow is determined based on an input from the airflow sensor at 923. In response to the present airflow, the CPU 788 determines at 922 the fan control signal 931 that needs to be output based on the received inputs 911 or 912. Upon determination of, for example, a difference between the input from the airflow sensor 923 and an input received from either 911 or 912, the CPU 788 may output a fan control signal 931.

Figure 10:
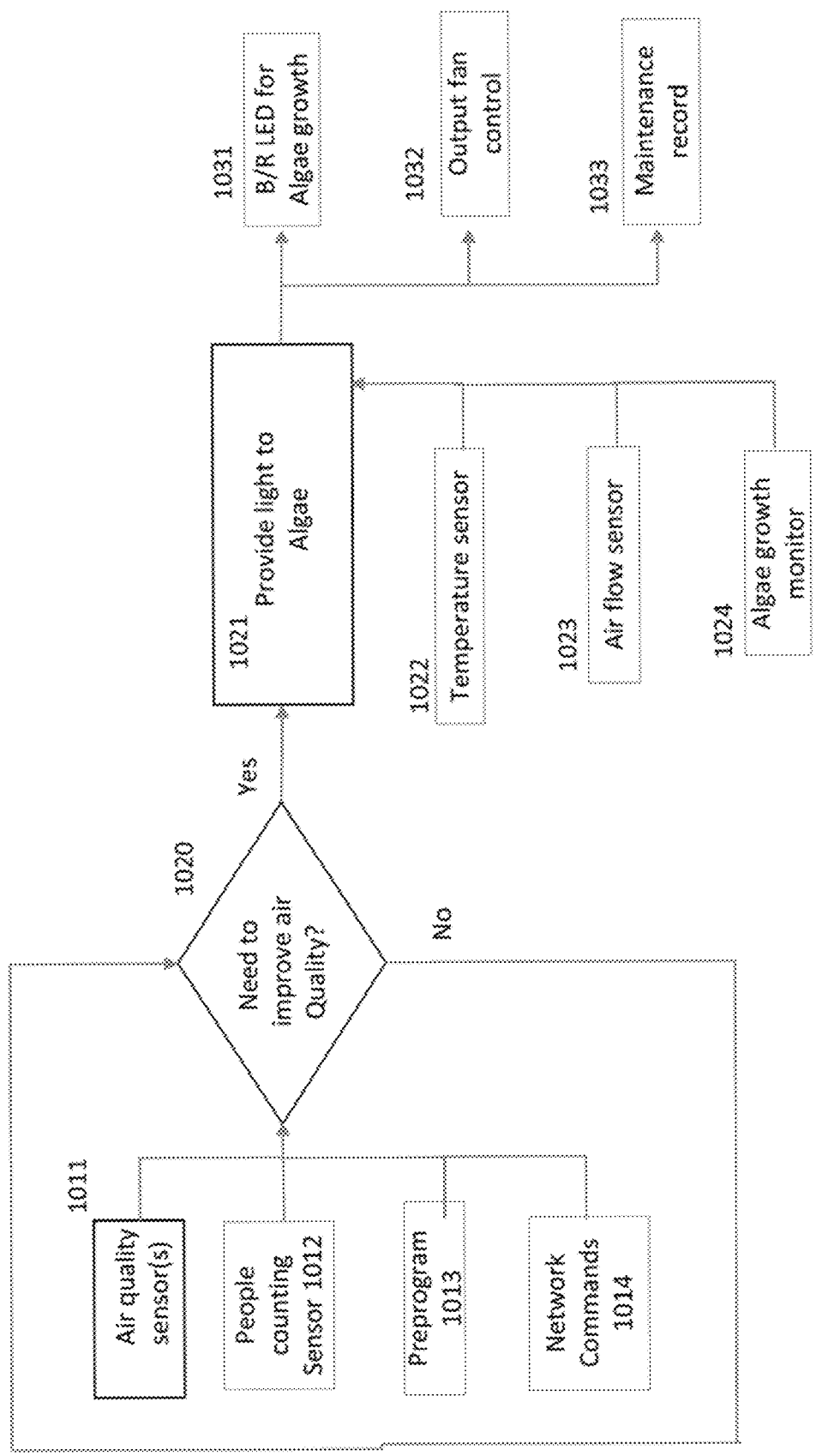
FIG. 10 illustrates another example of a control algorithm for determining whether the air quality in the proximity of the luminaire is satisfactory.

FIG. 10 illustrates another example of a control algorithm for determining whether the air quality in the proximity of the luminaire is satisfactory. In this example, the process 1000 is an example of a process that may be implemented upon execution of the programming in memory 799 by the CPU 788.

The CPU 788 may review the inputs from the air quality sensors 1011, occupancy (e.g., people counting) sensors 1012, preprogramming 1013, or network commands 1014 to determine, at 1010, whether there is a need to improve air quality, such as in the vicinity of luminaire at 1020. If the determination is NO, there is no need to improve air quality, the CPU 788 may continue to review inputs received via 1011 to 1014. Conversely, if the determination is YES, there is a need to improve air quality based on the inputs from any of 1011-1014, the CPU 788 may process the received signal(s) from the respective input to activate the algae at 1021 from a dormant state. For example, the algae within the luminaire may be in a dormant state until the algae is provided with access to/is exposed to light and $CO_2$ in order to proceed through photosynthesis. Once photosynthesis begins, the algae likely enters a growth phase. The growth phase can be partially controlled by the exposure of the algae to its optimum wavelength of light. The exposure to the light and $CO_2$ of the algae at 1021 may be dependent upon inputs from the temperature sensor 1022, the air flow sensor 1023, or an algae growth monitor 1024. Upon entering the growth phase (or occurrence of photosynthesis) of the algae at 1021, the CPU 788 may output signals related to modulation of the blue (B) and red (R) LEDs for algae growth and photosynthesis, output fan control 1032 or a maintenance record 1033. The signals output by the CPU 788 may be control signals for the B/R LEDs and that may control the B/R LEDs to operate according to preset commands. Examples of present commands may include controlling the B/R LEDs to provide approximately twelve (12) hour light/dark cycles for normal algae growth functions, or limited light for implementing, for example, a reduced rate of algae growth.

While the above examples are described with reference to a luminaire with a biofilter in which the biofilter is configured to treat the air that contact the biofilter, the luminaire may also be equipped with both a biofilter and a biosensor. A biosensor may be a device that provides an observable or detectable response to the presence of a toxin. Examples of such a biosensor are described in Applicant's contemporaneously filed patent application entitled Luminaire with Biosensor (Ser. No. 15/986,190), the entire contents of which are incorporated herein by reference.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A luminaire, comprising:
   a housing;
   a light source arranged in the housing of the luminaire and including multiple light sources configured to illuminate a space, wherein at least one of the multiple light sources emits general illumination light in the space,
   a biofilter arranged within the housing of the luminaire and configured to treat air in the space, and
   an air circulation system configured to draw the air into contact with the biofilter and output the air treated by contact with the biofilter into at least a portion of the space below the air circulation system and the housing of the luminaire and illuminated by the light source,
   wherein the biofilter comprises:
      a substrate which is permeable to air,
      a microorganism arranged on the substrate and configured to treat the air, and
      an air permeable membrane located on an outer surface of the substrate,
      wherein another of the multiple light sources is configured as a biofilter light source to illuminate the microorganism on the substrate of the biofilter.

2. The luminaire of claim 1, wherein the biofilter is capable of removing carbon dioxide from the air.

3. The luminaire of claim 1, wherein the biofilter is capable of adding oxygen to the air.

4. The luminaire of claim 1, wherein the biofilter is capable of removing carbon dioxide from the air and capable of adding oxygen to the air.

5. The luminaire of claim 1, wherein the biofilter is capable of removing a volatile organic compound from the air.

6. The luminaire of claim 1, wherein the biofilter is capable of adding an odor to the air.

7. The luminaire of claim 1, wherein the microorganism is capable of photosynthesis.

8. The luminaire of claim 1, wherein the microorganism is a bacteria or algae.

9. The luminaire of claim 1, wherein the substrate further comprises a support for the microorganism.

10. The luminaire of claim 9, wherein the support further comprises glass particles, ceramic particles, gravel particles, plastic particles, activated charcoal, or a combination thereof.

11. The luminaire of claim 9, wherein the support further comprises a hydrogel.

12. The luminaire of claim 1, wherein the substrate further comprises compost, soil, heather, or peat.

13. The luminaire of claim 1, further comprising an additional light source which is capable of illuminating the microorganism.

14. The luminaire of claim 1, wherein the air circulation system comprises a fan.

15. A system, comprising:
the luminaire of claim 1, and
a controller coupled to control light from the light source and the air circulation system.

16. The luminaire of claim 1, wherein the biofilter light source emits light in at least one of a wavelength of 450-495 nanometers or 620-750 nanometers.

17. A method, comprising:
(1) emitting light from a light source arranged in a housing of a luminaire, wherein the light source includes multiple light sources configured to illuminate a space, and wherein at least one of the multiple light sources emits general illumination light in the space,
(2) drawing air, via an air circulation system, into contact with a biofilter arranged within the housing of the luminaire, wherein the biofilter treats the air, and
(3) outputting the air treated by contact with the biofilter into at least a portion of the space below the air circulation system and the housing of the luminaire illuminated by the light source,
wherein the biofilter comprises:
a substrate which is permeable to air,
a microorganism arranged on the substrate and configured to treat the air, and
an air-permeable membrane located on an outer surface of the substrate,
wherein another of the multiple light sources is configured as a biofilter light source to illuminate the microorganism on the substrate of the biofilter.

18. The method of claim 17, wherein the biofilter removes carbon dioxide from the air and adds oxygen to the air or removes a volatile organic compound from the air.

19. The method of claim 17, wherein the microorganism is a bacteria or algae.

20. The method of claim 17, wherein the biofilter light source emits light in at least one of a wavelength of 450-495 nanometers or 620-750 nanometers.

* * * * *